United States Patent
Cao

(10) Patent No.: US 7,572,803 B2
(45) Date of Patent: Aug. 11, 2009

(54) HYDRATED CRYSTALLINE ESTERS OF CAMPTOTHECIN

(75) Inventor: Zhisong Cao, Friendswood, TX (US)

(73) Assignee: The Christus Stehlin Foundation for Cancer Research, Houston, TX (US)

( * ) Notice: Subject to any disclaimer, the term of this patent is extended or adjusted under 35 U.S.C. 154(b) by 131 days.

(21) Appl. No.: 11/923,727

(22) Filed: Oct. 25, 2007

(65) Prior Publication Data

US 2009/0111845 A1    Apr. 30, 2009

(51) Int. Cl.
*A61K 31/4745* (2006.01)
*C07D 491/22* (2006.01)

(52) U.S. Cl. .......................... 514/283; 546/48

(58) Field of Classification Search .............. 514/283; 546/48
See application file for complete search history.

(56) References Cited

U.S. PATENT DOCUMENTS

| | | | |
|---|---|---|---|
| 5,352,789 A | 10/1994 | Hinz | |
| 5,527,913 A | 6/1996 | Hinz | |
| 5,552,154 A | 9/1996 | Giovanella et al. | |
| 5,608,066 A | 3/1997 | Hinz | |
| 5,652,244 A | 7/1997 | Giovanella et al. | |
| 5,731,316 A | 3/1998 | Cao et al. | |
| 5,889,017 A | 3/1999 | Giovanella et al. | |
| 5,922,877 A | 7/1999 | Cao | |
| 5,968,943 A | 10/1999 | Cao et al. | |
| 6,080,751 A | 6/2000 | Stehlin et al. | |
| 6,096,336 A | 8/2000 | Cao et al. | |
| 6,107,486 A | 8/2000 | Hinz | |
| 6,120,793 A | 9/2000 | Cao et al. | |
| 6,156,897 A | 12/2000 | Hinz | |
| 6,166,029 A | 12/2000 | Giovanella et al. | |
| 6,218,399 B1 | 4/2001 | Cao et al. | |
| 6,228,855 B1 | 5/2001 | Cao et al. | |
| 6,342,506 B1 | 1/2002 | Giovanella et al. | |
| 6,352,996 B1 | 3/2002 | Cao et al. | |
| 6,407,118 B1 | 6/2002 | Cao et al. | |
| 6,407,239 B1 | 6/2002 | Cao et al. | |
| 6,624,170 B2 | 9/2003 | Giovanella et al. | |
| RE38,408 E | 1/2004 | Cao | |
| 6,699,875 B2 | 3/2004 | Cao et al. | |
| 6,703,399 B2 | 3/2004 | Cao et al. | |
| 2001/0031761 A1 | 10/2001 | Cao et al. | |

OTHER PUBLICATIONS

International Search Report and Written Opinion of the International Search Report for corresponding International Patent Application No. PCT/US2008/081047 dated Jan. 29, 2009 (14 pages).
Cao et al., "Alkyl Esters of Camptothecin and 9-Nitrocamptothecin: Synthesis, in vitro Pharmacokinetics, Toxicity, and Antitumor Activity," Journal of Medicinal Chemistry, 1998, vol. 41, No. 1, pp. 31-37.
U.S. Appl. No. 11/833,031, filed Aug. 2, 2007, Cao.

*Primary Examiner*—Charanjit S Aulakh
(74) *Attorney, Agent, or Firm*—Kilyk & Bowersox, P.L.L.C.

(57) ABSTRACT

Hydrated crystalline camptothecin esters, such as crystalline aliphatic ester hydrates of camptothecin, pharmaceutical compositions containing crystalline aliphatic ester hydrates of camptothecin, methods of treating a cancer or malignant tumor using the crystalline camptothecin ester hydrates and methods of making the same are described.

19 Claims, 5 Drawing Sheets

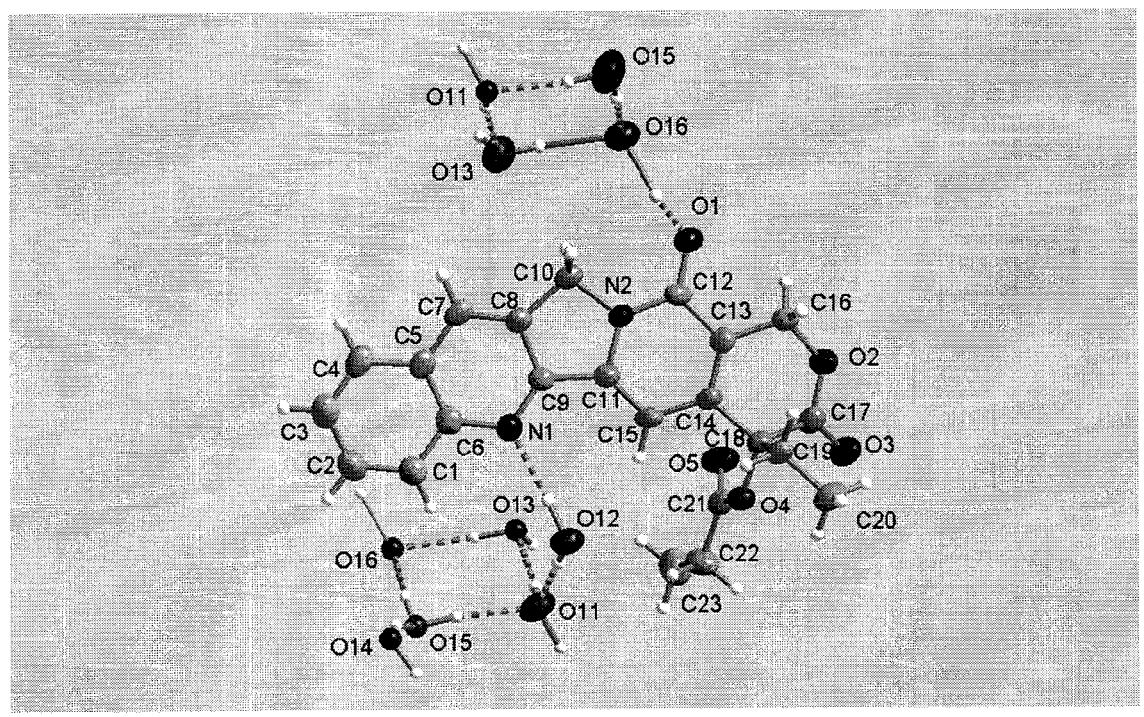
Fig. 1. Molecular Structure of $C_{23}H_{20}N_2O_5 \cdot 3H_2O$

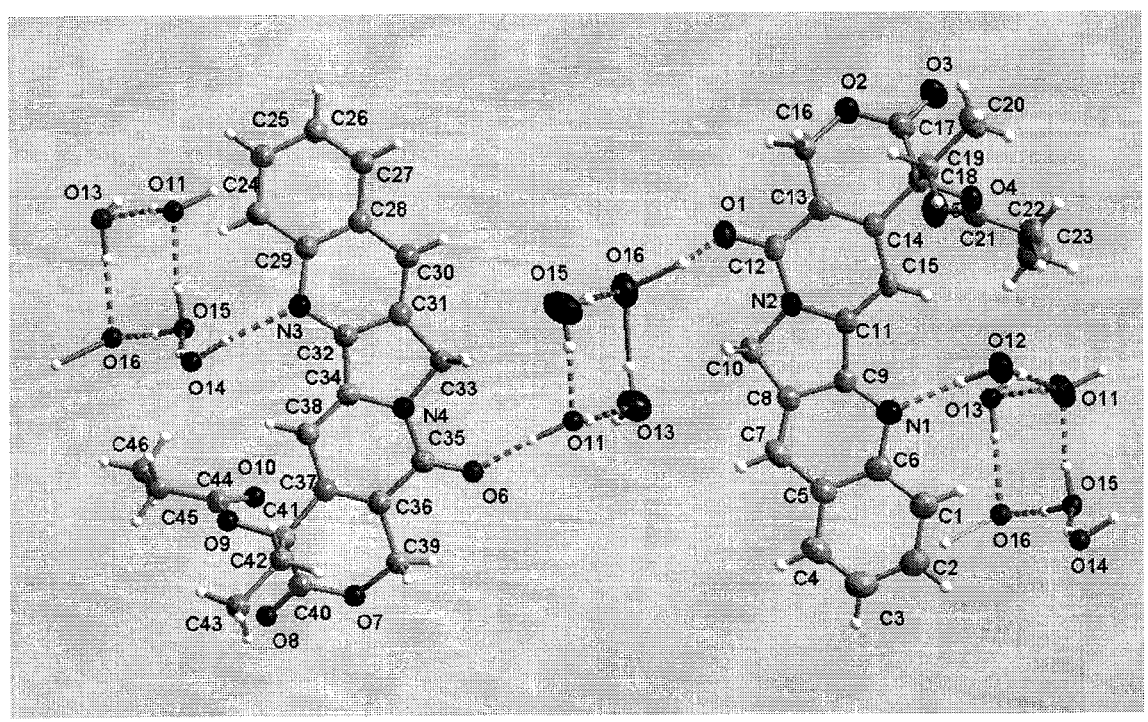
Fig. 2. H$_2$O bridged Molecular Structure of
2 x C$_{23}$ H$_{20}$ N$_2$ O$_5$·3H$_2$O

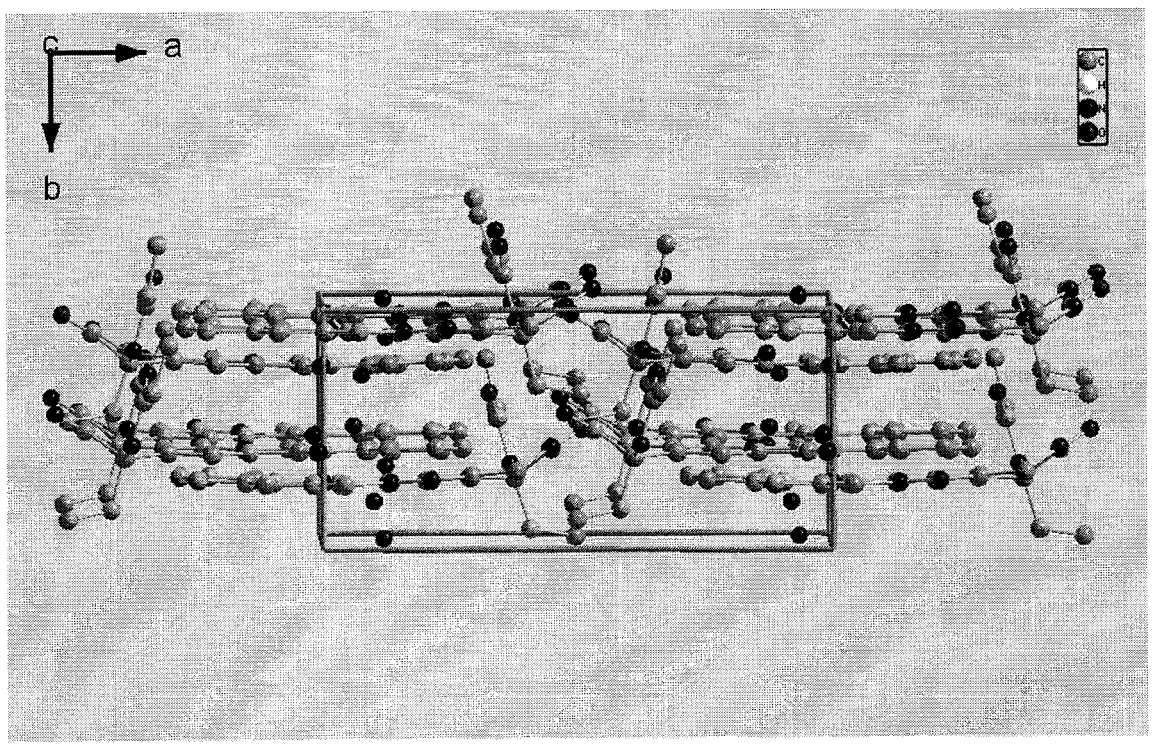
Fig. 3. Three Dimentional Crystal Structure of $C_{23} H_{20} N_2 O_5 \cdot 3H_2O$ (a,b-dimentions)

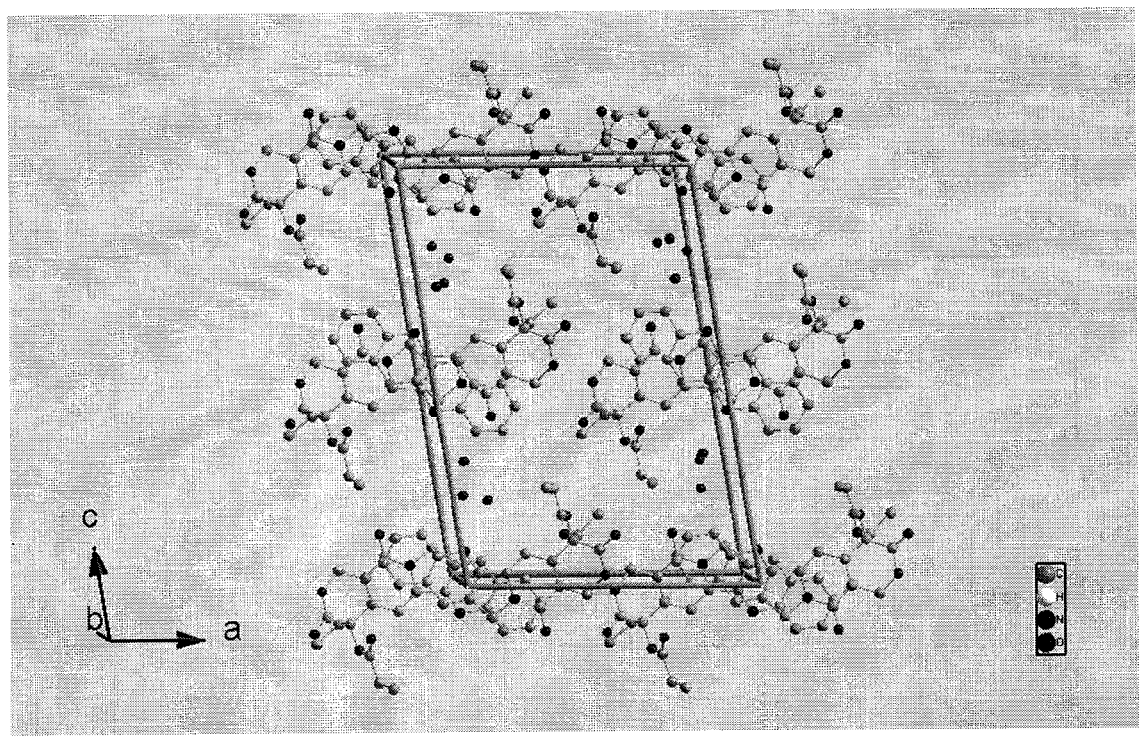
Fig. 4. Three Dimentional Crystal Structure of $C_{23}H_{20}N_2O_5 \cdot 3H_2O$ (a,c-dimentions)

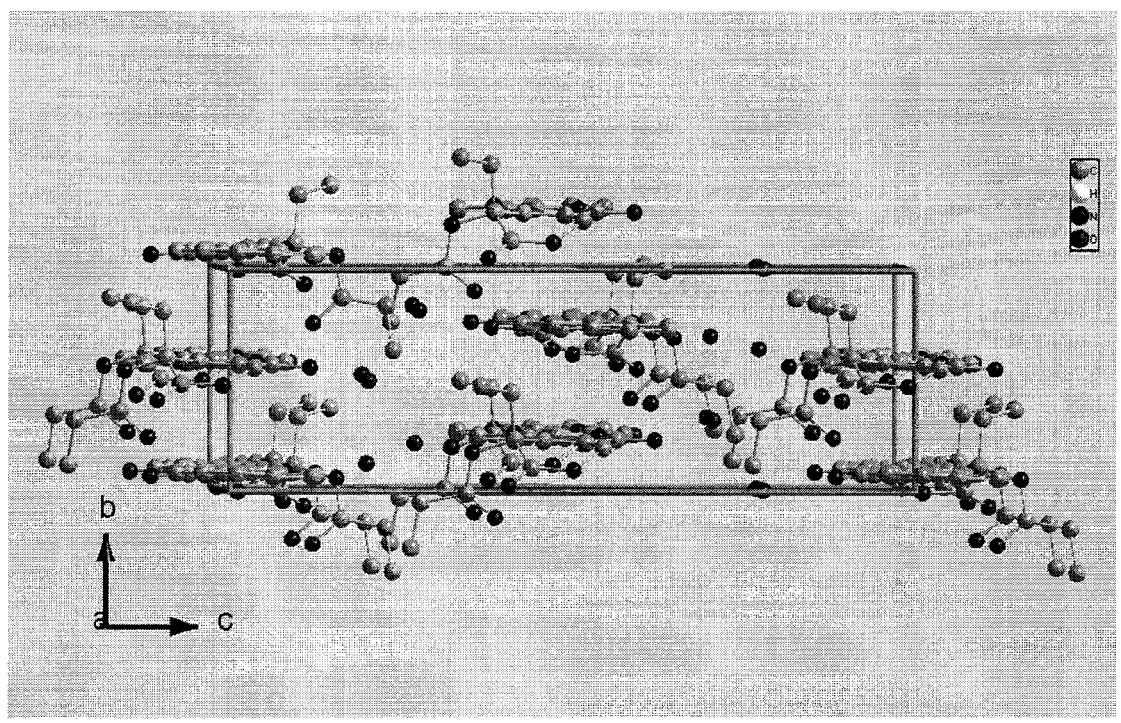
Fig. 5. Three Dimentional Crystal Structure of $C_{23} H_{20} N_2 O_5 \cdot 3H_2O$ (b,c-dimentions)

HYDRATED CRYSTALLINE ESTERS OF CAMPTOTHECIN

FIELD OF THE INVENTION

The present invention relates to esters of camptothecin and using the esters of camptothecin for treating cancer, malignant tumors, and the like.

BACKGROUND OF THE INVENTION

The toxicity (or side effects) that patients suffer as a result of anti-cancer drugs taken during the process of chemotherapy remains the biggest enemy associated with cancer treatment. The therapeutic index (TI) of an anti-cancer agent is defined as a ratio of the most tolerated dose to the effective dose. It is known that most anti-cancer agents clinically used today have a very narrow TI range (1 to 1.2). In other words, the toxic effects of most anti-cancer agents in patients receiving chemotherapy are unavoidable at the effective dose levels because of the narrow therapeutic index associated with the anti-cancer agents. The differences in toxicity between agents are the grades of severity and types of suffering. Fluorouracil (5-FU) is one of the most commonly used chemotherapeutic agents for the systemic and palliative treatment of patients with cancers arising from the gastrointestinal tract, breast, head, and neck. Dihydropyrimidine dehydrogenase (DPD) is the initial and rate-limiting enzyme in the catabolism of 5-FU. A DPD deficiency is increasingly recognized as an important pharmacogenetic disorder in the etiology of severe 5-FU associated toxicity. It has been reported that cancer patients who were genetically heterozygous or homozygous for a mutant allele of the gene encoding DPD suffered from severe toxicity, including death, following the administration of 5-FU. Van Kuilenburg A B P, Haasjes J, Richel D J et al. *Clinical implications of dihydropyrimidinedehydrogenase (DPD) deficiency in patients with severe 5-fluorouracil-associated toxicity: identification of new mutations in the DPD gene*. Clinical Cancer Res 2000, 6: 4705-4712. Van Kuilenburg A B P, Muller E W, Haasjes J et al. *Lethal outcome of a complete dihydroprimidine dehydrogenase (DPD) deficiency after administration of 5-fluorouracil: frequency of the common IVS14+1G>A mutation causing DPD deficiency*. Clin Cancer Res 2001, 7: 1149-1153. Platinum agents are also commonly used for treatment. A substantial body of literature documents the side effects of platinum compounds. Cisplatin has multiple toxicities: nephrotoxicity, neurotoxicity, ototoxicity, nausea and vomiting. DeVita V T, Hellman S, and Rosenberg S A. Cancer, *Principles and Practice of Oncology*, 7$^{th}$ Ed, Lippincott Williams & Wilkins 2005, 335. The nephrotoxicity of cisplatin almost led to its abandonment, until the introduction of aggressive hydration by Cvitkovic and his coworkers, which prevented the development of acute renal failure. Cvitkovic E, Spaulding J, Bethune V, et al. *Improvement of cis-dichlorodiamineplatinum (NSC 119875): therapeutic index in an animal model*. Cancer 1977, 39, 1357. Hayes D, Cvitkovic E, Golbey R, et al. *High dose cis-platinum diamine dichloride: amelioration of renal toxicity by mamnitol diuresis*. Cancer 1977, 39, 1372. The toxicity of cisplatin was considered by some to be a driving force in history both in the search for less toxic analogues and for more effective treatment for its side effects. Myelosuppression, which is not usually severe with cisplatin, is the dose-limiting toxicity of carboplatin. Evens B, Raju K. Calvert A, et al. *Phase II study of JM8, a new platinum analogue, in advanced ovarian carcinoma*. Cancer Treat. Rep., 67, 997, 1983. The dose-limiting toxicity of oxaliplatin is sensory neuropathy—a characteristic of all DACH-containing platinum derivatives. DeVita V T, Hellman S, and Rosenberg S A. Cancer, *Principles and Practice of Oncology*, 7$^{th}$ Ed, Lippincott Williams & Wilkins 2005, 335. Alkylating agents also play important roles in cancer treatments. Each alkylating agent is associated with a specific toxicity and is not discussed individually. The following toxicities are common to the alkylating agents as a class: hematopoietic toxicity, gastrointestinal toxicity, gonadal toxicity, pulmonary toxicity, alopecia, teratogenicity, carcinogenesis, and immunosuppression. DeVita V T, Hellman S, and Rosenberg S A. Cancer, *Principles and Practice of Oncology*, 7$^{th}$ Ed, Lippincott Williams & Wilkins 2005, 335. The usual dose-limiting toxicity for an alkylating agent is hematopoietic toxicity. Topoisomerase-interactive agents have increasingly gained attentions from clinical oncologists for their unique action mechanism. Toptecan is a semi-synthetic product from natural-occurring 10-hydroxycamptothecin and is indicated in the second-line treatment of advanced refractory ovarian, and small cell lung cancers, and it also has been active in the treatment of hematologic malignancies, including myelodysplastic syndromes and multiple myeloma. Huinink W, Gore M, Carmichael J, et al. *Topotecan versus paclitaxol for the treatment of recurrent epithelial ovarian cancer*. J Clin Oncol 1997, 15, 2183; Schiller J H, Adak S, Cella D, et al. *Topotecan versus observation after cisplatin plus etoposide in extensive-stage small-cell lung cancer: E7593-a phase II trial od the Eastern Cooperative Oncology Group*. J Clin Oncol 2001, 19, 2114; von Pawel J, Schiller J H, Shepherd F A, et al. *Topotecan versus cyclophosphamide, doxorubicin, and vincristine for the treatment of recurrent small-cell lung cancer*. J Clin Oncol 1999, 17, 658, Pizzolato J F, Saltz L B. *The camptothecins*. Lancet 2003, 361, 2235. The dose-limiting toxicity of this agent is myelosuppression. Although topotecan has been combined with a variety of other treatments, including radiation, cisplatin, paclitaxol, and doxorubicin in clinical trials, none of these combinations has achieved any routine use in clinical oncology. This may be due, in part, to the frequent myelosuppresive toxicity of topotecan that has made it difficult to combine in high doses with other bone marrow-suppressive agents. Miller A A, Lilenbaum R C, Lynch T J, et al. *Treatment-related fatal sepsis from topotecan/cisplatin and topotecan/paclitaxol*. J Clin Oncol 1996, 14, 1964. Irinotecan is also a semi-synthetic product from camptothecin family. This compound is indicated as a single agent or in combination with florouracil and leucovorin in treating patients with colorectal cancers and also found active in small cell lung cancer when given in combination with cisplatin. This combination has been found active in non-small cell lung cancer as well. Saltz L B, Cox J V, Blanke C, et al. *Irinotecan plus florouracil and leucovorin for metastatic colorectal cancer*. Irinotecan study group. N Engl J Med 2002, 343, 905; Douillard J Y, Cunningham D, Roth A D, et al. *Irinotecan combined with florouracil compared with florouracil alone as first-line treatment for metastatic colorectal cancer: a multicenter randomized trial*. Lancet 2000, 355, 1041; Pizzolato J F, Saltz L B. *The camptothecins*. Lancet 2003, 361, 2235. The dose-limiting toxicities of irinotecan are neutropenia and delayed-onset diarrhea, and its uses in clinical oncology are thus limited too. All other miscellaneous anti-cancer agents, including recently marketed erbitux and avastin, may be used for a limited number of specific treatments, but are also associated with toxicities. Thus, it is still a great challenge for cancer researchers and clinical oncologists to find better agents with a wider therapeutic index for treatment.

Camptothecin, a cytotoxic alkaloid first isolated from the wood and bark of *Camptotheca Acuminata* (Nyssaceae) by Wall and his coworkers (*J. Am. Chem. Soc.* 88, 3888, 1966), was shown to have antitumor activity against the mouse leukemia L 1210 system. The structure of camptothecin, an alkaloid which has a commonly occurring indole alkaloid group (Heckendorf et al., *J. Org. Chem.* 41, 2045, 1976), is shown below as Formula (X).

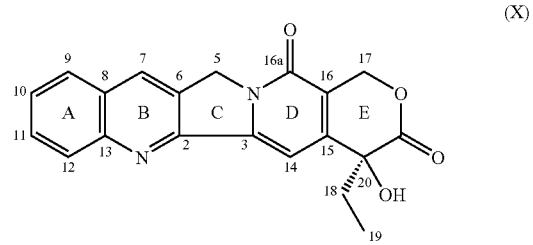

This compound ("CPT") has a pentacyclic ring system with only one asymmetrical center in ring E with a 20(S)-configuration. The pentacyclic ring system includes a pyrrolo [3, 4-b] quinoline moiety (rings A, B and C), a conjugated pyridone (ring D), and a six-membered lactone (ring E) with an α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (*Chem. Rev.* 23, 385, 1973, *Cancer Treat. Rep.* 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al., *Cancer Chemother. Rep.* 54, 461, 1970, and 56, 103, 1972, Muggia et al., *Cancer Chemother. Rep.* 56, 515, 1972, Moertel et al., *Cancer Chemother. Rep.* 56, 95, 1972, and Schaeppi et al., *Cancer Chemother. Rep.* 5:25, 1974). These results caused the discontinuation of phase I trials. Continued evaluation of this agent showed that the sodium carboxylate salt is only 10% as potent as the native camptothecin with the closed lactone ring intact (Wall et al., *In International Symposium on Biochemistry And Physiology of The Alkaloids*, Mothes et al., eds., *Academie—Verlag*, Berlin, 77, 1969, Giovanella et al., *Cancer res.* 51, 3052, 1991). In addition, important parameters for antitumor activity in the camptothecin family have been established (Wall et al., *Ann. Rev., Pharmacol Toxicol* 17, 117, 1977). These results indicate that an intact lactone ring E and α-hydroxyl group are essential for antitumor activity.

In the middle 1980s it was found that the molecular target of camptothecins was the novel nuclear enzyme topoisomerase I. Hsiang Y H, Liu L F. *Identification of mammalian DNA topoisomerase I as an intracellular target of anticancer drug camptothecin*. Cancer Res 1988, 48, 1722. At approximately the same time, several new water-soluble camptothecin derivatives, including two compounds (topotecan and irinotecan) discussed earlier, were prepared and biologically evaluated. The subsequent clinical evaluations of the two compounds demonstrated the predictable toxicities and meaningful anticancer activity. Takimoto C H, Arbuck S G. *Topoisomerase I targeting agents: the camptothecins*. In: Chabner B A, Longo D L, eds., Cancer therapy & biotherapy: principles and practice, 3$^{rd}$ ed. Philadelphia: Lippincott Williams & Wilkins 2001, 579. Topotecan was approved in 1996 as second-line treatment for advanced ovarian cancer, and it later gained the indication for treating patients with refractory small cell lung cancer. At exactly the same time, irinotecan was registered for treating 5-florouracil-refractory advanced colorectal cancer. This actually represented the first new agent to gain approval for treating this disease in the United States in nearly 40 years.

In 1989, Giovanella et al. found that some of the non-water soluble derivatives of camptothecin have high antitumor activity against xenografts of human tumors (Giovanella et al., *Science*, 246, 1046, 1989). It was also shown that administration of camptothecin with closed lactone ring is superior to injections of water-soluble carboxylate salt (Giovanella et al., *Cancer Res.*, 51, 3052, 1991). These findings further confirmed the importance of the intact lactone ring to biological activity.

Ring opening of 20(S)-camptothecin leads to much more potent anticancer activity in mice than in humans. In effect, CPT administered intramuscularly ("i.m.") subcutaneously ("s.c."), and intrastomach ("i.s.") has proven to be a very potent anticancer agent against human tumors in mice, i.e., when growing as xenotransplants in nude mice (Giovanella et al., *Cancer Res.* 51:3052, 1991). However, when tumors were treated with CPT in humans, a lower degree of anticancer activity in humans, than in mice, was exhibited (Stehlin et al., *In Camptothecins: New Anticancer Agents*, 1995, CRC Press, pp. 59-65).

The same phenomenon was observed with other CPT-derivatives. In mice, 9-nitrocamptothecin ("9NC") has proven to be 2-3 times more potent than CPT against human tumor xenografts causing the total eradication of all the human malignancies treated (Pantazis et al., *Cancer Res.* 53:1577, 1993; Pantazis et al., *Int. J. Cancer* 53:863, 1995).

Ring opening is particularly problematic in that camptothecins exist in two distinct forms. The naturally-occurring camptothecin has an S-configuration and is 10 to 100 times more biologically active than the R-isomer. The S-configured lactone form is thought to be required for anti-tumor activity, and the carboxylate form usually relates to clinical toxicities. The molecule exists in equilibrium in aqueous solution. This equilibrium is pH-dependent. At physiological pH, i.e., 7 or above, the equilibrium equation is as follows:

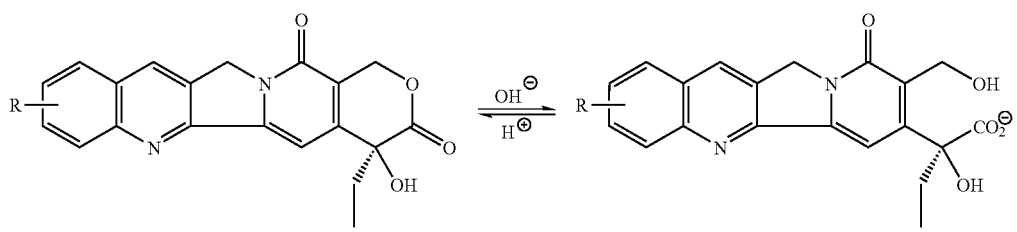

The hydrolysis reaction of the biological active lactone ring of camptothecins with water at higher pH gives the biologically inactive open form. Additionally, the hydrolysis problem with CPT and its analogs is exacerbated in human blood because the predominant human serum albumin (HSA) preferentially binds to the carboxylate form, which shifts the lactone/carboxylate equilibrium toward the inactive form (*J. Biochem.*, 212, 285-287, 1993; *Biochemistry*, 33, 10325-10336, 1994; *Biochemistry*, 33, 12540-12545, 1994). Accordingly, preserving the lactone ring of the molecule for a sufficient time for the tumor cells to cycle through the S-phase is a major challenge and has been the focus of a considerable amount of research.

A number of attempts have been made to provide derivatives of camptothecin having greater biological activity and enhanced stability. Many of these compounds are the products of modifications on the A, B, and C rings of the molecule, but few of these modifications have enhanced the stability of the lactone ring under physiological conditions. Other approaches have been more successful. For instance, acylating of 20-OH group provides a useful tool for the protection of lactone ring E. Wall et al., U.S. Pat. No. 4,943,579, describes several acylated camptothecin compounds having water solubility, although the lactone may not remain intact under physiological conditions. U.S. Pat. No. 5,968,943 to Cao et al. discloses CPT-derivatives which are effective anti-tumor agents.

A number of different reactions are reported in literature for preparing camptothecin esters.

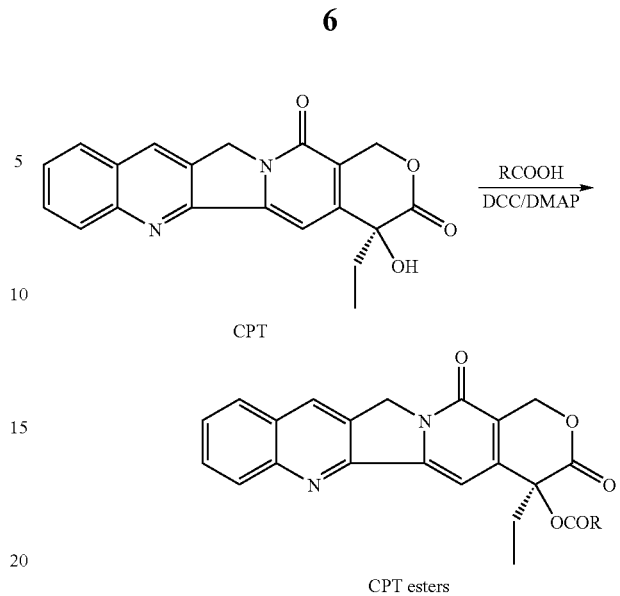

Direct acylation of camptothecin with organic acid anhydrides with pyridine as catalyst was employed for preparing alkyl and alkenyl camptothecin esters (as shown above). This reaction usually gives high yields, but the availability of organic acid anhydrides restricts the scope of the reaction.

A dicyclohexylcarbodiimide (DCC)/dimethylaminopyridine (DMAP) reagent system was therefore, used for acylation reactions of carboxylic acids with alcohols and thiols. Previously, a method was used to prepare aromatic camptothecin esters (as shown below).

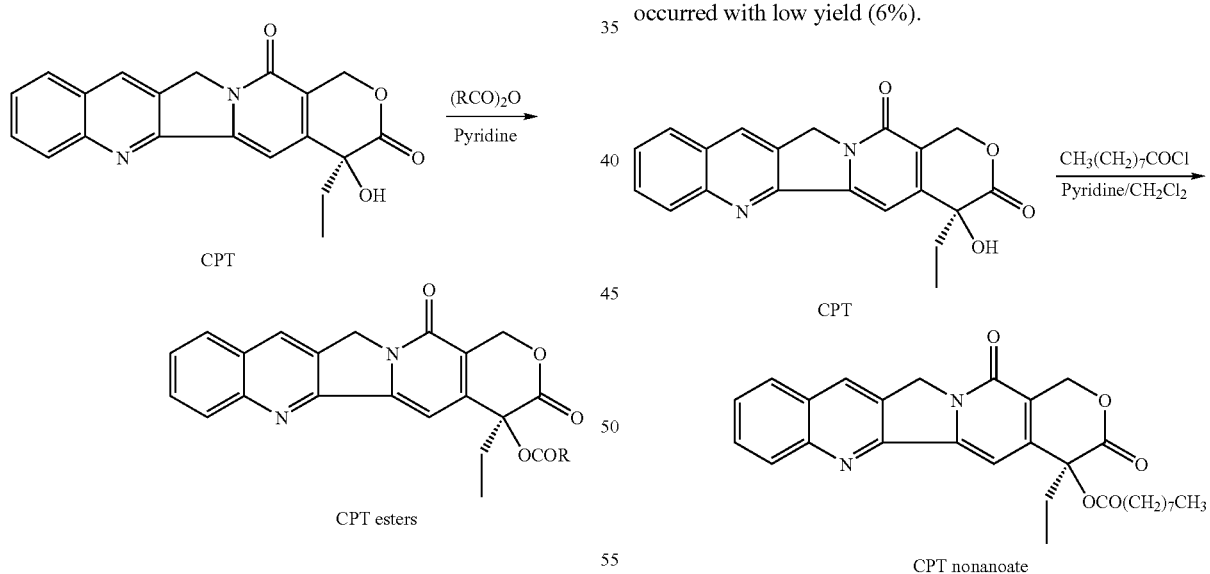

This procedure, however, gives good reaction yields only when the carboxylic acids are very electrophilic. When the acids are less electrophilic, the reaction gives low yield or no expected product at all. For example, when using propionic acid to prepare camptothecin propionate with this procedure, the ester product was essentially not obtained and the starting camptothecin was almost 100% recovered.

Nonanoic chloride was also used as an acylating agent to esterify camptothecin with pyridine as an HCl-trapping agent in methylene chloride. The reaction (as shown below) occurred with low yield (6%).

As the inherent structural features of camptothecin provide an ideal platform for cancer researchers to modify the structure for obtaining better anti-cancer agents, many different camptothecin esters have been synthesized and evaluated. It has been found that the esterification products largely increased the biological life of the molecules in the body. It has also been shown that treatment of human tumors grown in xenografts in nude mice with synthetic camptothecin esters is effective, and toxicity in mice is minimal. Cao, Z.; Pantazis, P.; Mendoza, J.; Early, J.; Kozielski, A.; Harris, N.; Vardeman, D.; Liehr, J.; Stehlin, J.; Giovanella, B. *Ann. N.Y. Acad. Sci.* 2000, 922, 122; Cao, Z.; Pantazis, P.; Mendoza, J.; Early, J.; Kozielski, A.; Harris, N.; Giovanella, B. *Acta Pharmacologica Sinica* 2003, 24, 109.

While many methods for preparing camptothecin esters exist, however, each procedure has certain restrictions as discussed above. Therefore, there is still a need to develop camptothecin esters which retains the anti-tumor activity of the mother compound, CPT, has much lower toxicity than CPT, and which can be produced by alternative procedure(s) for preparing camptothecin esters.

SUMMARY OF THE PRESENT INVENTION

Accordingly, a feature of the present invention is to provide a crystalline camptothecin ester hydrate which demonstrates a broad spectrum of anti-tumor activity and preferably low or no observable toxicity.

Another feature of the present invention is to provide a crystalline camptothecin ester hydrate having a wider therapeutic index range than most anti-cancer agents used today.

Another feature of the present invention is to provide a safe and simple method for preparing a crystalline camptothecin ester hydrate.

A further feature of the present invention is to provide crystalline camptothecin ester hydrates which retain significant antitumor activity as does the mother compound, CPT, and have much lower toxicity than its mother compound.

Yet another feature of the present invention to provide crystalline camptothecin ester hydrates possessing good absorbability in the living body.

To achieve the features and in accordance with the purposes of the present invention, as embodied and broadly described herein, the present invention, in part relates to crystalline camptothecin ester hydrates, such as crystalline aliphatic ester hydrates of camptothecin, like crystalline camptothecin-20-O-propionate ("CZ48") hydrate, pharmaceutical compositions comprising crystalline aliphatic ester hydrates of camptothecin, methods of treating a cancer or malignant tumor using the crystalline camptothecin ester hydrates and methods of making the hydrated crystalline camptothecin esters comprising reacting a camptothecin compound with at least one acylating agent protonated by at least one acid.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

All patents, applications, and publications mentioned throughout the application are incorporated in their entirety by reference herein and form a part of the present application.

It is to be understood that both the foregoing general description and the following detailed description are exemplary and explanatory only and are intended to provide a further explanation of the present invention, as claimed.

BRIEF DESCRIPTION OF THE DRAWINGS

FIG. 1 is an ORTEP diagram of a single molecule of the product.

FIG. 2 is an ORTEP diagram showing two molecules of crystalline camptothecin-20-O-propionate hydrate linked together by a water bridge.

FIG. 3 is an ORTEP diagram showing the three-dimensional structure (a,b dimensions) of crystalline camptothecin-20-O-propionate hydrate.

FIG. 4 is an ORTEP diagram showing the three-dimensional structure (a,c dimensions) of crystalline camptothecin-20-O-propionate hydrate.

FIG. 5 is an ORTEP diagram showing the three-dimensional structure (b,c dimensions) of crystalline camptothecin-20-O-propionate hydrate.

DETAILED DESCRIPTION OF THE PRESENT INVENTION

Camptothecins ("CPTs") have considerable anti-tumor and anti-cancer activity, but these compounds are susceptible to degradation under normal physiological conditions, and the metabolites produced often exhibit toxic properties. The metabolism studies of camptothecin in human plasma carried out in the laboratory showed that the only metabolite detected is the ring-opened sodium carboxylate salt which is toxic and inactive. The measurement of pharmacokinetics for CPT in human plasma indicates that the half-life time of the drug with the lactone ring intact is about 30 min. These results imply that the drug will lose 90% of its activity and produce a lot of toxicities in a very short time after the patients take it.

According to the present invention, CPT, converted into a more lipo-soluble and hydrated crystalline ester molecule, hereinafter at times, called a prodrug, is disclosed. When taken by patients, the prodrugs are rapidly introduced into the bloodstream of the patients and are readily converted to the parent compound in the body. It is noted that the prodrug itself can be active as well, and/or can be partially or fully converted.

According to various embodiments, the compounds of the present invention can comprise crystalline aliphatic esters of CPT in hydrated form having the formula

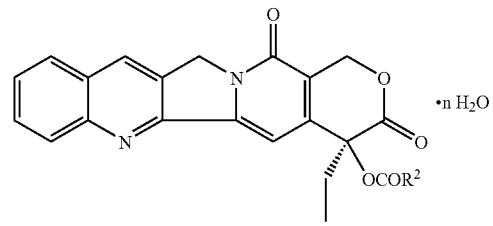

In this formula, n can represent any number ranging from 1 to 10 or more, such as 1, 2, 3, 4, 5, 6, 7, 8, 9, or 10. $R^2$ represents a $C_2$-$C_6$ alkyl group, such as a $C_2$-$C_4$ alkyl group. In one or more embodiments, $R^2$ is —$CH_2CH_3$; —$CH_2CH_2CH_3$; —$CH_2CH_2CH_2CH_3$; or —$CH_2CH_2CH_2CH_2CH_2CH_3$. As one more specific embodiment, n represents 3 and $R^2$ is —$CH_2CH_3$ or —$CH_2CH_2CH_3$ According to at least one embodiment, the compounds of the present invention can comprise crystalline camptothecin-20-O-propionate hydrate having the formula shown below:

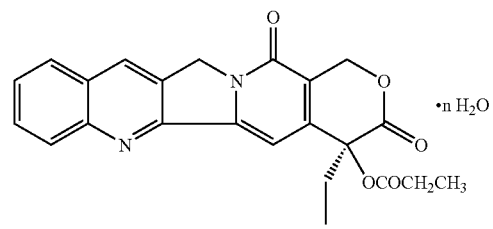

In this formula, n can represent any number ranging from 1 to 10, such as 1, 2, 3, 4, 5, 6, 7, 8, 9, or 10.

As an example, the structure of crystalline camptothecin-20-propionate hydrate was determined by single crystal X-ray analysis, and is shown in FIGS. 1-5. FIG. 1 shows the ORTEP diagram of a single molecule of the product. One molecule of camptothecin-20-O-propionate and about 3 molecules of water link together through strong hydrogen bonds. More than one molecule of camptothecin-20-O-propionate in a crystal unit can be linked to each other through a bridge made of $H_2O$ molecules. FIG. 2 shows two molecules of camptothecin-20-O-propionate linked together by a water bridge. FIGS. 3-5 show the three-dimensional structures of the crystal. Other CPT esters of the present invention will have the same structure except for the ester-chain length.

The prodrugs of the present invention can be in a liquid or solid state. According to the present invention, the compounds are crystalline. According to at least some embodiments, the compounds of the present invention can be crystalline or a solid in which the constituent atoms, molecules, or ions are packed in a regularly ordered, repeating pattern extending in all three spatial directions. The crystals can be a monoclinic system with sizes of $(0.10$ to $0.50) \times (0.01$ to $0.10) \times (0.01$ to $0.05)$ mm$^3$ and volumes of from 100 to 5000 Å$^3$, such as volumes of from 200 to 4500 Å$^3$ or from 500 to 4000 Å$^3$, or from 750 to 3500 Å$^3$, or from 1000 to 3000 Å$^3$, or from 1250 to 2500 Å$^3$ or from 1500 to 2200 Å$^3$.

As used herein, "crystalline" refers to a material that contains a specific compound, which may be hydrated and/or solvated, and has sufficient crystal content to exhibit a discernable diffraction pattern by XRPD or other diffraction techniques. Often, a crystalline material that is obtained from a solvent by direct crystallization of a compound dissolved in a solution or interconversion of crystals obtained under different crystallization conditions, will have crystals that contain the solvent, termed a crystalline solvate. Examples of crystal properties include orientation of the chemical moieties of the compound with respect to each other within the crystal and predominance of a specific form of the compound, which is favored by the presence of an acid in the solvent composition.

According to at least one embodiment, the compounds of the present invention can have a purity of from about 90% to about 100% by AUC (area under curve). According to some embodiments, the compounds of the present invention can have a purity of from about 95% to about 100% by AUC. According to at least one embodiment, the compounds of the present invention can have a purity of from about 99% to about 100% by AUC, such as from 99.3% to 99.999%; 99.5% to 99.999%; 99.75% to 99.999%; 99.85% to 99.999%, all by AUC. According to at least one embodiment, the compounds of the present invention can have a melting point of from about 240° C. to about 243° C., such as 242° C. or about 242° C. This melting point(s) is especially preferred for the crystalline ester hydrate where $R^2$ is $—CH_2CH_3$. The melting points of the compounds of the present invention can be lower or higher than the above range when $R^2$ is a $CH_3$ or $C_3H_7$ or $C_4H_9$ or $C_6H_{13}$ group.

According to various embodiments, the present invention can comprise crystalline aliphatic ester hydrates of CPT having an S-configuration, an R-configuration, and/or racemic mixtures of both S- and R-isomers. According to some embodiments, the crystalline aliphatic ester hydrates of CPT derived from the natural camptothecin has only an S-configuration or primarily an S-configuration, such as 90% or higher, 95% or higher, 98% or higher, 99% or higher, or 99% to 99.99%.

Conversion of the prodrugs to the mother compound, CPT, can be mediated by a group of enzymes called esterases present in the blood of many animals, including humans. Since the prodrugs are rapidly distributed throughout the body in a short period of time after delivery, these compounds exist at a very low concentration at the time they undergo enzymatic hydrolysis by which the mother camptothecin is released, which prevents CPT from precipitating in the bloodstream.

Therefore, the present invention provides hydrated crystalline CPT derivatives or analogues which preferably remain intact longer in a human or animal body, particularly in the human body, thus enhancing the anti-tumor and anti-cancer effects without producing undesirable side effects.

The present invention also provides pharmaceutical compositions containing a pharmaceutically effective amount of one or more compounds of the present invention optionally in combination with one or more pharmaceutically acceptable carriers, excipients, diluents or adjuvants. For example, compounds of the present invention may be formulated in the form of tablets, pills, powder mixtures, capsules, injectables, solutions, suppositories, emulsions, dispersions, food premix, and in other suitable forms. They may also be manufactured in the form of sterile solid compositions, for example, freeze-dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use of parenteral administration.

Typical of pharmaceutically acceptable carriers are, for example, manitol, urea, dextrans, lactose, non-reducing sugars, potato and maize starches, magnesium stearate, talc, vegetable oils, polyalkylene glycols, ethyl cellulose, poly(vinylpyrrolidone), calcium carbonate, ethyloleate, isopropyl myristate, benzyl benzoate, sodium carbonate, gelatin, potassium carbonate, silicic acid. The pharmaceutical preparation may also contain non toxic auxiliary substances such as emulsifying, preserving, and/or wetting agents, and the like as for example, sorbitan monolaurate, triethanolamine oleate, polyoxyethylene monostearate, glyceryl tripalmitate, dioctyl sodium sulfosuccinate, and the like.

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An "excipient" can refer to an inert substance added to a pharmacological composition to further facilitate administration of a compound. Examples of excipients include but are not limited to calcium carbonate, calcium phosphate, various sugars and types of starch, cellulose derivatives, gelatin, fats, lipids, vegetable oils and polyethylene glycols.

A "pharmaceutically effective amount" can also or alternatively mean an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of the active compound of the invention. Daily doses can be from about 0.05 mg/kg to about 20 mg/kg or from about 0.1 mg/kg to about 10 mg/kg.

In some embodiments, the preferred therapeutic effect is the inhibition, to some extent, of the growth of cells characteristic of a proliferative disorder, e.g., breast cancer or pancreatic cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

The pharmaceutical compositions used in the methods of the instant invention can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain sweetening agents, flavoring agents, coloring agents and/or preserving agents. Tablets can contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions can contain the active material in admixture with excipients suitable for the manufacture of aqueous suspensions. Such excipients can be suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may he preserved by the addition of an anti-oxidant such as ascorbic acid.

The compounds and pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and/or antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an compound or composition of the invention can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods, compounds and compositions of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

One aspect of the invention is a pharmaceutical composition useful for treating cancer in a warm-blooded animal, which composition comprises at least one compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the $18^{th}$ or $19^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose can contain a therapeutically effective amount sufficient to treat cancer in a subject and may contain from about 1.0 to 1000 mg of compound, for example about 50 to 500 mg.

The compound can be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 50 to about 500 mg of a compound of the present invention.

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Compositions according to the current invention can be prepared so that an oral dosage unit form contains between about 5 to about 50% by weight (% w) in dosage units weighing between 50 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a perservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

The compound may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and should, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In some cases, e.g., where a compound of the invention is quite water insoluble, it may be useful to provide liposomal delivery. The system restrains the compound of the invention by incorporating, encapsulating, surrounding, or entrapping the compound of the invention in, on, or by lipid vesicles or liposomes, or by micelles.

In one or more embodiments of the present invention, the present invention relates to methods to treat various forms of cancer, malignant tumors, and/or precursors of cancer or precursors of malignant tumors. The method can include treating a cancer or a malignant tumor in a patient by administering the compound or a composition containing the compound of the present invention. The method can include administering an effective amount of the compound or a composition containing the compound of the present invention to treat the cancer or malignant tumor, wherein the cancer or malignant tumor is responsive to the treatment using the compound or composition containing the compound of the present invention. As described further below, various cancers and malignant tumors can be treated with the present invention. The compounds of the present invention are effective in treating human or animal patients for cancers, malignant tumors, neoplasms, or cancer precursors. Specific examples include, but are not limited to, leukemia, melanoma, liver, breast, colorectal, rectal, ovary, prostate, stomach, bladder, desmoplastic small round cell tumor (DSRCT), pancreas, lung, kidney, colon, central nervous system tumors, or any combination thereof. As used herein, the term "malignant tumor" is intended to encompass all forms of human or animal carcinomas, sarcomas and melanomas which occur in the poorly differentiated, moderately differentiated, and well differentiated forms.

Another important feature of the compounds of the present invention relates to the relatively low or no apparent overall toxicity of the prodrugs administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

The crystalline aliphatic ester hydrates of CPT demonstrate a broad spectrum of activity with no observable toxicity in mice at variable dose ranges. The therapeutic index can be determined by testing in nude mice, such as the average therapeutic index from testing mice having a tumor xenograft that is a cancer tumor of bladder, breast, colon, kidney, lung, melanoma, pancreas, prostate, ovarian, and/or any of the cancers mentioned herein. Further, the therapeutic index of this agent is tremendously improved compared with most anti-cancer agents clinically used today by oncologists. The therapeutic index of the crystalline aliphatic ester hydrates of CPT can range from 2 to 500 (e.g., 3 to 500, 4 to 50, 3 to 10, 4 to 15, 5 to 20, 8 to 20, 10 to 20, 25 to 500, 50 to 500, 75 to 500, 100 to 500, 150 to 500, 200 to 500, 250 to 500, 300 to 500, 350 to 500, 400 to 500, 450 to 500) when 2000 mg/kg is considered to be the most tolerated dose. The therapeutic index for most anti-cancer agents currently used in clinical oncology, however, is approximately 1, which is very narrow. Further, none of the anti-cancer agents currently used can be continuously used for a long duration at the effective dose. The compounds of the present invention can be continuously used on a daily or weekly or monthly basis for 2 months, 3 months to 12 months, 4 months to 15 months, 5 months to 15 months, 6 months to 24 months, or more.

According to various embodiments, the crystalline aliphatic ester hydrates of CPT, may be administered in combination with pharmaceutically acceptable carriers or diluents. For example, such pharmaceutical compositions may routinely contain, e.g., pharmaceutically acceptable salts, buffering agents, preservatives and/or compatible carriers. As used herein, "pharmaceutically acceptable carrier" refers to one or more compatible solid or liquid filler, diluent or encapsulating substances which are suitable for administration to mammals including humans. A pharmaceutically acceptable carrier can be, for example, one or more gelatin capsules, cholesterol pellets, micro suspensions in lipid and in lipid-like emulsions (Intralipid 10, Intralipid 20, or natural oils), or other suitable emulsifiers for lipophilic compounds. The amount of an active ingredient (crystalline aliphatic ester hydrates of CPT) contained in the pharmaceutical composition according to the invention may vary depending upon many factors such as the administration route and the types of targets (e.g., types of cancer) the compounds are used against.

In treating or retarding malignant tumors in mammals in accordance with the present invention, the compounds or pharmaceutical compositions thereof of the present invention are administered by means known to those skilled in the art, such as, intramuscularly, intravenously, transdermally, or orally. Commonly known methods, for example, gelatin capsules for oral administration, as well as formulations such as micro suspensions in lipid and in lipid-like emulsions (e.g. —Intralipid 20, cottonseed oil and peanut oil) for intramuscular administration and inclusion in cholesterol pellets for subcutaneous long-term administration can be used. Another method of administering the compounds of the present invention is by a transdermal or transcutaneous route. One example of such an embodiment is the use of a patch. In particular, a patch can be prepared with a fine suspension of a compound disclosed in the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the CPT hydrate of the present invention in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

As used herein, an "effective amount" of the compounds of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/$M^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537-538 (1970)). An effective amount of the camptothecin compounds in the present invention can range from about 10 to about 1000 mg/$m^2$ of body surface per day.

The preferred effective amounts or dosages of the compounds or prodrugs of the present invention are about 1 to about 100 mg Prodrug/kg of body weight twice a week for an intramuscular route and about 1 to about 500 mg Prodrug/kg/day for the oral route. Effective amounts or dosages of CPT derivatives or Prodrugs of the present invention are, for instance, about 1 mg/kg/week to about 1.00 mg/kg/week of the Prodrug for the transdermal route. For all of the administering routes, the exact timing of administration of the dosages can be varied to achieve optimal results. Generally, when using Intralipid 20 as the carrier for the prodrug, the actual dosage of prodrug reaching the patient will be less. This is due to some loss of the prodrug on the walls of the syringes, needles and preparation vessels, which is prevalent with the Intralipid 20 suspension. When a carrier, such as cottonseed oil is used, this above-described loss is not so prevalent because the prodrug does not adhere as much to the surfaces of syringes, needles, preparation vessels, and the like. For instance and preferably, it has been found that generally about 2.5 mg Prodrug/kg of body weight twice per week using cottonseed oil, administered by an intramuscular route, will deliver the same amount to the patient as 4.0 mg Prodrug/kg of body weight twice per week using Intralipid 20 as a carrier. Generally, about 1 mg to about 4 mg of prodrug is added to about 0.1 ml to about 1 ml of carrier.

In one or more embodiments of the present invention, one or more compounds of the present invention (or a composition containing the compound(s) of the present invention) can be solubilized in liposomes. The liposomes may include, for example, lipids such as cholesterol, phospholipids, or micelles comprised of surfactant such as, for example, sodium dodecylsulfate, octylphenolpolyoxyethylene glycolt, or sorbitan mono-oleate. Typically, the prodrugs bind to the lipid bilayer membrane of the liposome with high affinity. The liposome bound prodrug can preferably intercalate between the acyl chains of the lipid. The lactone ring of the camptothecin-derivative, membrane-bound prodrug is thereby removed from the aqueous environment inside and outside of the liposome and thus protected from hydrolysis. Since the liposome-bound drug is protected from hydrolysis, the antitumor activity of the drug is preserved. For the camptothecin prodrugs which have a lower affinity for the liposome membrane and thus disassociate from the liposome membrane to reside in the interior of liposome, the pH of the interior of the liposomes may be reduced thereby preventing hydrolysis of the camptothecin prodrugs.

A group of liposomal delivery systems that can be used in accordance with the present invention include those described in U.S. Pat. Nos. 5,552,156 and 5,736,156, which are herein incorporated in their entireties by reference. Other liposomal delivery systems which may be employed in accordance with the present invention include liposomes containing active agents aggregated with lipids or surfactants as described in U.S. Pat. Nos. 5,827,533 and 5,882,679; lipid vesicles formed with alkyl ammonium fatty acid salts as described in U.S. Pat. No. 5,874,105; liposomes for encapsulating active agent dry powder compositions as described in U.S. Pat. No. 5,783,211; liposomal drug delivery systems for topical patches as described in U.S. Pat. No. 5,718,914; the liposomes described in U.S. Pat. No. 5,631,237; the liposome and lipid complex compositions described in U.S. Pat. Nos. 5,549,910 and 5,077,057; the liposomes used for sustained release of steirodial drugs as described in U.S. Pat. No. 5,043,165; the liposomes described in U.S. Pat. No. 5,013,556; and the liposomes described in U.S. Pat. No. 4,663,161; all of which are herein incorporated in their entireties by reference.

Unilamellar liposomes, also referred to as single lamellar vesicles, are spherical vesicles comprised of one lipid bilayer membrane which defines a closed compartment. The bilayer membrane is composed of two layers of lipids; an inner layer and an outer layer. The outer layer of lipid molecules are oriented with their hydrophilic head portions toward the external aqueous environment and their hydrophobic tails pointed downward toward interior of the liposome. The inner layer of lipid lays directly beneath the outer layer; the lipids are oriented with their heads facing the aqueous interior of the liposome and their tails toward the tails of outer layer of lipid.

Multilamellar liposomes, also referred to as multilamellar vesicles are composed of more than one lipid bilayer membrane, which membranes define more than one closed compartment. The membranes are concentrically arranged so that the different membranes are separated by compartments much like an onion skin.

As used herein the phrase "liposomal prodrugs" means either that some or all of the camptothecin prodrug is located in one or more of the compartments of a liposome or micelle, or the camptothecin prodrug is bound to the membrane of the liposome. The delivery systems can be a liposome comprising a lipid bilayer membrane which entraps a camptothecin prodrug. As used herein, the phrase "bound to lipid membrane" means that at least the lactone ring of some or all of the camptothecin prodrug binds to the lipid membrane of the liposome, and where the liposome contains more than one bilayer membrane the camptothecin prodrug is bound to at least 1 membrane. Those camptothecin prodrugs that have a high affinity for such membrane tend to remain bound to the membrane. Those camptothecin prodrugs with a low affinity for the liposome membrane, will at least partially disassociate from the liposome membrane and reside in the liposome compartment.

Micelles as defined herein are spherical receptacles comprised of a single, monolayer membrane which defines a closed compartment and the membrane is comprised of surfactant molecules oriented so that the hydrocarbon tails are oriented toward the compartment and the polar head portions are oriented toward the external aqueous environment. The camptothecin prodrugs, when associated with micelles, are either in the compartment, bound to the micelle membrane, or bound to the outside surface of the micelle.

Liposomes have been used successfully to administer medications to cancer patients, and have been shown to be useful clinically in the delivery of anticancer drugs such as doxorubicin, daunorubicin, and cisplatinum complexes. Forssen, et al., Cancer Res. 1992, 52: 3255-3261; Perez-Soler, et al. Cancer Res. 1990, 50: 4260-4266; and, Khokhar, et al. J. Med. Chem. 1991, 34: 325-329, all of which are incorporated herein in their entireties by reference.

Similarly, micelles have also been used to deliver medications to patients, (Brodin et al., Acta Pharm. Suec. 19 267-284 (1982)) and micelles have been used as drug carriers and for targeted drug delivery, (D. D. Lasic, Nature 335: 279-280 (1992); and, Supersaxo et al., Pharm. Res. 8: 1286-1291 (1991)), including cancer medications, (Fung et al., Biomater. Artif. Cells. Artif. Organs 16: 439 et. seq. (1988); and Yokoyama et al., Cancer Res. 51: 3229-3236 (1991)), all of which are incorporated herein in their entireties by reference.

The liposomes and/or micelles of the present invention containing the camptothecin prodrugs can be administered to a cancer patient, typically intravenously. The liposomes and/or micelles are carried by the circulatory system to the cancer cells where the membrane of the vesicle fuses to the membrane of the cancer cell thereby releasing the camptothecin prodrug to the cancer cell, or where the liposomes and/or micelles remain adjacent to the cancer cells, the camptothecin prodrug diffuses from the liposomes and/or micelles to be taken up by the cancer cells.

Any lipid or mixture of lipids which forms liposomes and/or micelles is suitable for use in the present invention. Phosphatidylcholines, including, for example, L-α-dimyristoylphosphatidylcholine (DMPC), L-α-dipalmitoylphosphatidyleholine (DPPC) and L-α-distearoylphosphatidylcholine (DSPC) are suitable. Also, phosphatidylglycerols, including, for example, L-α-dimyristoylphosphatidylglycerol (DMPG) are suitable. The DMPC and DMPG are both fluid phase at 37° C., while DSPC is solid phase at 37° C. Since the presence of negatively charged lipid in the liposome membrane causes the liposomes to repel each other, small amounts, such as, for example about 10%, of an negatively charged lipid, such as distearolphosphotidylglycerol (DSPG), may be incorporated into the DSPC liposomes. Other suitable phospholipids include: phosphatidyl-ethanolamines, phosphatidylinositols, and phosphatidic acids containing lauric, myristic, palmitic, palmitoleic, stearic, oleic, linoleic, arachidonic, behenic and lignoceric acid. Another suitable lipid includes cholesterol.

The liposomes and/or micelles may be coated with polyethyleneglycol or GM, protein which assists the particles in avoiding the reticuloendothelial system.

DSPC, since it is solid phase at 37° C., (the average temperature of humans), limits the diffusion of the camptothecin drug from the liposome and thus can be employed to time release the camptothecin prodrugs.

The DMPG, DPPC, and DSPC could be obtained from Avanti Polar Lipids, Alabaster, Ala. and used without further purification. All other chemicals can be reagent grade and used without further purification.

Any surfactant or mixtures thereof, which forms micelles is suitable for use in the present invention. Suitable surfactants include sodium dodecylsulfate (SDS) available from Kodak, Rochester, N.Y., octylphenolpolyoxyethylene glycol, available under the trade name "Triton X-100" from Aldrich Chemical Co., Milwaukee, Wis., and sorbitan mono-oleate, available under the trade name "Polysorbate 80" and "Tween 80" from Sigma Chemical Co. Other suitable surfactants include, for example, deoxycholic acid sodium salt, cholic acid sodium salt, and polyoxyethylene-10-cetylether, available under the trade name "BRIJ-56"; these surfactants are available from Sigma Chemical Co.

In addition, micelles may be composed of lipid, such as phospholipid, and mixtures of lipids. Also micelles may be composed of both lipid and surfactant.

Liposome suspensions can be prepared by the method of Burke and Tritton Biochemistry 24: 1768-1776 (1985), which is incorporated herein in its entirety by reference. The liposomes are preferably small unilamellar vesicles (SUV), rather than multilamellar vesicles (MLV). However, both SUVs and MLVs are within the scope of the invention. While MLVs have the advantage of limiting the rate of diffusion of the associated camptothecin prodrug, they have the disadvantage of being more easily scavenged by macrophages than the SUVs. Stock lipid suspensions containing 200 mg/mL lipid in phosphate-buffered saline (PBS) containing 8 mM $Na_2HPO_4$, 1 mM $KH_2PO_4$, 137 mM NaCl, and 3 mM KCl having a pH of 7.4 can be used and are prepared by vortex mixing for 5-10 min above the gel-liquid-crystalline phase transition temperature $T_M$ of the lipid. The lipid suspensions are then sonicated using a bath-type sonicator from Laboratory Supplies Co., Hicksville, N.Y., for 3-4 hours until they become optically clear. A decrease in pH from 7.4 to 6.8 may be observed for the SUV preparations of DMPG; therefore, the pH of these SEV suspensions is preferably adjusted to 7.4 using small quantities of 2.5M NaOH in PBS and sonicated again. Each type of liposome suspension is preferably annealed for 30 minutes at 37° C.

The preparations of many liposomes and micelles are described in U.S. Pat. Nos. 5,552,156, 7,244,449, and 5,736,156, which are herein incorporated in their entireties by reference.

"Prodrugs" can be derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

The term "alkyl," alone or in combination, refers to an optionally substituted straight-chain, optionally substituted branched-chain, or optionally substituted cyclic alkyl radical having from 1 to about 6 carbons, more preferably 2 to 4 carbons. Examples of alkyl radicals include methyl, ethyl, n-propyl, isopropyl, n-butyl, isobutyl, sec-butyl, tert-butyl, tert-amyl, pentyl, hexyl, and the like. The term "cycloalkyl" embraces cyclic configurations, is subsumed within the definition of alkyl and specifically refers to a monocyclic, bicyclic, tricyclic, and higher multicyclic alkyl radicals wherein each cyclic moiety has from 3 to about 6 carbon atoms. Examples of cycloalkyl radicals include cyclopropyl, cyclobutyl, cyclopentyl, cyclohexyl and the like.

"Effective amount" or "effective dose" can refer to the amount necessary or sufficient to inhibit undesirable cell growth, e.g., prevent undesirable cell growth or reduce existing cell growth, such as tumor cell growth. The effective amount can vary depending on factors known to those of skill in the art, such as the type of cell growth, the mode and regimen of administration, the size of the subject, the severity of the cell growth, etc. One of skill in the art would be able to consider such factors and make the determination regarding the effective amount. This can be achieved with the present invention.

"Therapeutically effective antitumor therapy" can refer to a therapy which is effective to maintain or decrease the size, e.g., volume, of a primary tumor or metastatic tumor. This can be achieved with the present invention.

According to one or more embodiments of the present invention, methods are provided for making the crystalline aliphatic ester hydrates of camptothecin that include the step of reacting a starting camptothecin compound with at least one acylating agent protonated by at least one acid, such as, sulfuric acid. The acylating agent can contain the ester group to be formed on the starting camptothecin. The camptothecin ester produced is a crystalline aliphatic ester hydrates of CPT. In at least one embodiment, the camptothecin ester produced is crystalline camptothecin-20-O-propionate hydrate (CZ48 hydrate). According to at least one embodiment the starting camptothecin compound is CPT.

The amount of the starting camptothecin compound can be any desirable amount as long as sufficient acylating agent is present to convert at least a portion of the starting camptothecin to a ester of camptothecin as described herein. For example, the amount of the starting camptothecin compound can be from about 1 g to about 100 g, or more.

With respect to the acylating agent, the acylating agent generally in one or more embodiments, contains the ester group to be formed on the starting camptothecin. The acylating agent can be an organic acid derivative, such as an acid anhydride. For instance, the acylating agent can have the formula $(R^1CO)_2O$, wherein $R^1$ represents an organic group and generally the $R^1$ group is the group that forms the organic part of the ester attachment onto the starting camptothecin compound. More particularly, and for example purposes only, the $R^1$ group can be an alkyl group, such as a $C_1$-$C_6$ alkyl group. Specific examples of $R^1$ groups include, but are not limited to, —$CH_2CH_3$; —$CH_2CH_2CH_3$; —$CH_2CH_2CH_2CH_3$; or —$CH_2CH_2CH_2CH_2CH_2CH_3$.

The amount of acylating agent used in the reactions of the present invention can be an amount sufficient so that an ester group is formed on the starting camptothecin compound. Suitable amounts of the acylating agent include, but are not limited to, from about 10 mL to about 1 L, based on acylating 20 g to 30 g of starting camptothecin. The examples set forth below provide exemplary amounts of the acylating agent that can be used in the reaction.

With respect to the acid used in the reactions of the present invention, the acid can be used in catalytic amounts so that the acylation of the starting camptothecin can occur with the organic acid derivatives, such as the acid anhydride. The acid can be sulfuric acid or other acids such as HCl, $HNO_3$, or $HClO_4$. The acid can be concentrated acid such as concentrated sulfuric acid. The acid can have any molar strength, such as from about 0.0001 to about 0.02 M, or higher. The amount of acid used in the reaction can be a catalytic amount, such as from about 0.1 ml to about 1.0 ml and more preferably from about 0.20 ml to about 0.75 ml or about 0.5 ml per reaction with 20 g to 30 g of starting camptothecin. The amount of acid used to catalyze the esterification reaction can be varied depending on the scales of the reactions involved.

In the present invention, according to one or more embodiments, the various reactants can be combined together in any order, either sequentially, at the same time, or in any combination. Any reaction vessel can be used. The reaction can take place at any temperature above the freezing point of the reactants such as from about 20° C. or higher. The reaction can occur at ambient temperatures or elevated temperatures, such as from about 20° C. to about 110° C. or higher. The reaction can take place in a short order, such as from 1 minute to 1 hour or more. The reaction time depends upon the amount of reactant used, and the desirable amount of conversion of the starting CPT to camptothecin ester. The reaction can occur in inert atmospheres or in air. An example of an inert atmosphere can be a nitrogen atmosphere or argon atmosphere.

According to various embodiments, yield of the reaction can be at least 95% to 100% by weight of the starting camptothecin product which is converted to an ester of camptothecin. In at least one embodiment, the yield of the reaction is about 97% to 100% of the camptothecin product to an ester of camptothecin.

The purity and/or the concentration of the starting CPT or reactant is unimportant. Different purities and different concentrations may affect the percent yield of the esters of CPT that is formed from the reaction. Preferably, the purity of the starting CPT reactant is from about 30% to about 100%. More preferably, the purity is from about 80 to about 100% or 90% to 99.9% or higher. Preferably, the amount of CPT or CPT derivative reactants is from about 0.1 to about 50%, of the total volume of the reactants. More preferably, the amount is from about 0.5 to about 5.0%, of the total volume of the reactants.

The pH, the concentration, and the purity of the acid is not important, so long as the impurities in the acid do not react with the CPT or the acylating agent. The acidity of the acid should be strong enough to be able to protonate the acylating agent employed for the reaction. Strong inorganic acids, such as $H_2SO_4$, HCl, $HNO_3$, and $HClO_4$ have this ability. Other acids, such as $AlCl_3$ and $BF_3$ can be used for this type of catalytic esterification reaction. The pH of the acid can be from about 0.5 to about 5. Preferably, the acid is concentrated and is high in purity. For example, the concentration can be from about 60% to about 100%. Preferably, the concentration is from about 95% to about 98%. The purity of the acid can be from about 30% to about 100%. Preferably, the purity is from about 90 to about 100%. Preferably, the amount of acid, such as concentrated sulfuric acid, is from about 0.1 to about 10%, of the total volume of the reactants. More preferably, the amount is from about 0.5 to about 8.5%, of the total volume of the reactants.

Preferably, the acid is added to the mixture of the CPT and the acid anhydride while the mixture is being stirred. Preferably, the amount of acid that can be added to the mixture is sufficient for the acid to act as a catalyst. Preferably, about 4 to about 8 glass pipet drops of the acid can be added to about 70-100 ml of the acyl halide (A similar amount of acid can be used when the acylating agent is other than the acyl halide). However, if necessary, more or less acid can be added to the mixture of the CPT and the acid anhydride, preferably while the mixture is being stirred.

The mixture of CPT, acid anhydride and acid can be placed in a reactor, which preferably includes an inert atmosphere, such as $N_2$, and can be heated from about 80° C. to about 120° C. Preferably, the mixture is heated from about 90° C. to about 110° C. and more preferably, the reactor is heated to about 100° C.

Preferably, the reaction will run until the desired product is formed. The reaction time can be as short as several hours to as long as several days. Preferably, the reaction time can be about 15 hours under an inert atmosphere, such as $N_2$.

An example of the reaction is depicted in Scheme 1 below.

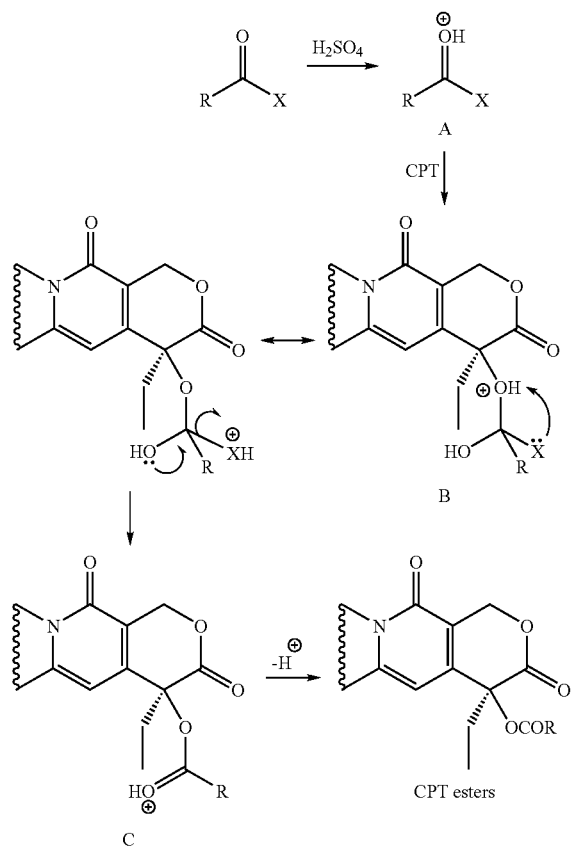

While not wishing to be bound by any theory, it is believed that the protonation of the acylating agent (RCOX) with an acid, such as sulfuric acid, forms a reactive intermediate A. Attaching a cationic carbonyl carbon of intermediate A with camptothecin forms an intermediate B. The subsequent elimination of a molecule of XH from B gives final ester products.

After completion of the reaction, which can be determined by a change in the color of the solution, the solution can be cooled to room temperature. The solvent can be removed by any commonly known separation methods, such as an evaporation method or a filtration method. The crude product obtained after removing the reaction solvents can be purified by refluxing in alcoholic solvents, such as ethanol. The final product is obtained in crystalline form upon recrystallization and/or reprecipitation from the alcohol.

New camptothecin esters with extremely reduced toxicity, while maintaining the antitumor activity, have been prepared, such as crystalline aliphatic ester hydrates of CPT, like crystalline camptothecin-20-O-propionate hydrate. According to one or more embodiments, the aliphatic ester of CPT can be prepared by $H_2SO_4$-catalyzed acylation reaction depicted in the reaction as shown below.

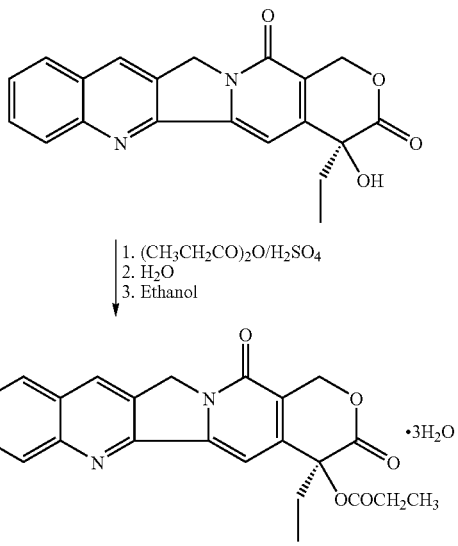

As is shown, the starting camptothecin can be reacted with propionic anhydride under catalyzation of concentrate sulfuric acid. The reaction mixture can then be quenched with excessive water to remove the un-reacted propionic anhydride and propionic acid formed from the reaction. The crystallization of the crude product from absolute ethanol (or other solvents, like other alcohols) gives the final crystalline camptothecin-20-O-propionate hydrate in almost quantitative yield. This would also be true for the other CPT esters of the present invention. It should be understood that the phrase "quantitative yield" as used herein, can include yields of 97%-100% by weight. The purity of the product obtained from the reaction is about 99%-100%. The melting point of the product is about 240° C.-243° C.

The present invention will be further clarified by the following examples, which are intended to be purely exemplary of the present invention.

EXAMPLES

Example 1

Crystalline camptothecin-20-propionate (CZ48) hydrate was prepared as follows. About 20 g camptothecin (0.05747 mole) and about 100 ml propionic anhydride (97%, Aldrich Chemical Co., Milwaukee, WD were added to a 200 ml round-bottomed flask equipped with a magnetic stirrer and a sand bath. The mixture was heated by sand bath while stirring. A few drops (8 to 10) of concentrate sulfuric acid (95-98%, A.C.S. reagent, Aldrich Chemical Co.) were added drop by drop when the sand bath temperature reached 80° C. The mixture was then stirred at 110±10° C. for overnight (~14 hr). After cooling down to room temperature, the reaction mixture was poured onto 1000 ml ice water portion by portion while stirring. After stirring for roughly 45 min, the mixture was filtrated. The residue obtained from filtration was allowed to air-dry for 24 hr. The dried crude product was transferred to a 500 ml round-bottomed flask equipped with a heating mantle.

To this crude product was added 200 ml absolute ethanol (99.5%, 200 proof, Aldrich Chemical Co.). The mixture was allowed to reflux for 2 hr, and then cooled to room temperature. The pure product was obtained as crystals after crystallization from ethanol. Purity was shown to be 99.8%, using high performance liquid chromatography (HPLC), and the melting point (mp) was determined to be 242° C. Dry nitrogen was routinely used as the reaction atmosphere in all reactions for the preparations. All glasswares were baked at 70+/−10° C. for a minimum of 2 h before being used. Melting points were obtained with a MEL-TEMP® melting point apparatus and were uncorrected. Camptothecin was purchased from The People's Republic of China and used as purchased.

In vivo anti-tumor activity determination. The human tumors used in the experiments discussed herein included 1 bladder line, 3 breast lines, 4 colon lines, 1 DSRCT line, 1 kidney line, 2 melanoma lines, 2 lung lines, 7 pancreatic lines, and 1 prostate line. The hydrated crystalline CZ48 drug was finely suspended in cottonseed oil and stored in a refrigerator for using. The suspension was orally administered to the mice bearing human tumors once a day continuously for 5 days on and 2 days off or once a day for seven days for the whole treatment period. The treatment period for the various tumor lines varied, ranging from two weeks to one year. Of these tumor lines tested, 18 lines achieved positive response, in other words, greater than 50% inhibition in tumor-growth inhibition, with 5 days-on and 2 days-off schedule, and 2 pancreatic tumor lines failed to obtain the positive response. With the continuous schedule (daily treatment), one of those two negatively responded pancreatic tumor lines under the 5/2 schedule achieved the positive response. Table 1 summarizes the results.

TABLE 1

Antitumor activity of hydrated crystalline CZ48 against human xenografts in nude mice

| Tumors | | Colon | Breast | Lung | Melanoma | Pancreas | Bladder | DSRCT |
|---|---|---|---|---|---|---|---|---|
| Response | Positive[a] | 4/4 | 3/3 | 2/2 | 2/2 | 6/7 | 1/1 | 1/1 |
| | Negative[b] | | | | | 1/7 | | |

[a]Positive response means the inhibtion of growth bigger than 50%.
[b]Negative response means the inhibition of growth smaller than 50%.

While a positive response is defined as growth inhibition of at least 50%, in reality, complete growth inhibition was achieved for many tumor lines. The effective doses required to achieve the positive response varied depending on the types of tumors. For the CLO-breast carcinoma, the most sensitive tumor line from the tumor banks tested, complete inhibition was achieved with a low dose of hydrated crystalline CZ48 such as 4 mg/kg, whereas, CAK-kidney, PANC1-pancreasand SU86.86-pancreas, 3 of the less sensitive lines, required a dose as high as 1000 mg/kg to achieve the positive response. , Example 2

In vivo anti-tumor activity determination. All the animal experiments were performed on nude Swiss mice of the NIH, high-fertility strain. They were bred and raised in laboratory under strict pathogen-free conditions. For anti-tumor activity determination, a tumor xenograft growing in a nude mouse, approximately 1 cm³ in size, was surgically removed under sterile conditions, finely minced with iridectomy scissors, and suspended in cell culture medium at the ratio 1:10, v/v. One half of 1 mL of this suspension, containing about 50 mg of wet-weight tumor mince was subcutaneously inoculated on the upper half of the dorsal thorax of the mouse. Groups of four or five animals were used. Hydrated crystalline CZ48 was finely suspended in cottonseed oil and then injected into the stomach cavity of the mouse through the anterior abdominal wall using a 26 gauge needle. The weekly schedule used for oral administration of hydrated crystalline CZ48 was once a day for 7 days, or five days on and two days off. This schedule was employed throughout all the animal experiments. Treatment was initiated when the tumor had reached a volume of about 200 mm³, i.e., well-vascularized, measurable, and growing exponentially. Tumors growing in animals were checked and measured with a caliper once a week. The effective doses were established when a positive response in mouse was reached. The results are shown in Table 2.

TABLE 2

Effective doses of hydrated crystalline CZ48 in tumor lines

| Tumor lines | | Effective dose (mg/kg) | TI[a] |
|---|---|---|---|
| Bladder | BOL | 200 | 10 |
| Breast | CLO | 4 | 500 |
| | MUR | 300 | 7 |
| | WAR | 200 | 10 |
| Colon | HT29 | 50 | 40 |
| | McC | 300 | 7 |
| | SQU | 30 | 67 |
| | SW48 | 100 | 20 |
| DSRCT | MYE | 100 | 20 |
| Kidney | CAK | 1000 | 2 |
| Lung | DOY | 15 | 133 |
| | SPA | 100 | 20 |

TABLE 2-continued

Effective doses of hydrated crystalline CZ48 in tumor lines

| Tumor lines | | Effective dose (mg/kg) | TI[a] |
|---|---|---|---|
| Melanoma | BRO | 100 | 20 |
| | FOSS | 300 | 7 |
| Pancreas | ASPC1 | 300 | 7 |
| | HS766T | 100 | 20 |
| | LIE | 100 | 20 |
| | MiaPaCa2 | 100 | 20 |
| | PANC1 | 1000 | 2 |
| | SU86.86 | 1000 | 2 |
| Prostate | PC3P62 | 300 | 7 |

[a]TI was calculated assuming the most tolerated dose 2000 mg/kg

As shown in Table 2, crystalline camptothecin-20-O-propionate hydrate has a wide therapeutic index ranging from 2 for three tough lines to 500 for the most sensitive line (CLO-breast) if 2000 mg/kg is assumed to be the most tolerated dose.

Example 3

In vivo toxicity determination. Groups of 4 or 5 animals of about the same age and having similar weights were chosen and treated with crystalline CZ48 hydrate orally at doses of 1500 mg/kg and 2000 mg/kg, respectively, continuously for 60 days. The 3 groups of mice chosen for the toxicity studies were healthy, of similar age and weights, and non-tumor-bearing. One group was used as control, and the other two groups were treated with the drug at two high-dose levels, 1500 mg/kg and 2000 mg/kg respectively, for about two months. The body weight changes in animals during the treatment were recorded for the treated group versus the untreated group beginning at day 0 and ending at the 60$^{th}$ day. The results were shown in Table 3.

TABLE 3

Toxicity of crystalline CZ48 hydrate in nude mice[a]

| Days | Body weight (in grams) | | |
|---|---|---|---|
| | Control[b] | Dose 1 (1.5 g/Kg)[b] | Dose 2 (2.0 g/Kg)[b] |
| 0 (Starting date) | 32.0 (1.4) | 31.9 (2.0) | 32.3 (3.1) |
| 10 | 31.9 (1.5) | 30.4 (3.1) | 30.7 (4.3) |
| 21 | 32.2 (1.7) | 31.2 (1.9) | 31.2 (3.9) |
| 35 | 32.3 (2.1) | 32.3 (0.8) | 30.8 (3.2) |
| 45 | 32.1 (3.7) | 32.8 (1.7) | 31.7 (2.9) |
| 60 | 32.9 (1.7) | 33.0 (1.4) | 30.9 (3.3) |

[a]The scale used in determining the body weights is calibered and certified annually.
[b]The numbers in parentheses are SD Most strikingly, no noticeable toxicity in the treated mice was observed at any of the tested dose levels. The body-weight loss was used as a parameter to measure the toxicity of the agent. Usually, body weight loss of 10% or more in mice during treatment is considered a sign of toxicity. Greater body-weight loss signifies greater toxicity. The treatment did not result in significant body-weight loss, which implied that the dose levels employed were non-toxic to mice and also that the mice could tolerate the doses even higher than 2000 mg/kg. Continuous treatment with crystalline camptothecin-20-O-propionate hydrate in mice generated a wider therapeutic index range, and did not result in any noticeable toxicity.

Example 4

The determination of PK parameters of crystalline CZ48 hydrate. Pharmacokinetic profile of crystalline camptothecin-20-O-propionate hydrate with a single dose of 2000 mg/kg was recorded following an oral administration to nude mice. The corresponding $C_{max}$ and $T_{max}$ were 284.86±85.55 ng/mL and 2.0±0.0 h, respectively. Camptothecin-20-O-acetate, an analogue of CZ48 which was not a crystalline hydrate, was used as an internal standard for determining all PK parameters of the CZ48 hydrate. A 100 μL plasma from the mouse treated with crystalline CZ48 hydrate at dose of 2000 mg/kg was transferred into a 2-mL test-tube, and then 100 μL of internal-standard working solution (400 ng/mL) was also added to the tube. To the mixture, were also added 200 μL of 1% acetic acid solution and 1 mL ethyl ether. After vortex-mixing for 10 s, the mixture was incubated at room temperature on a shaker for 10 min, and then centrifuged at 10,000×g for 15 min. The upper layer obtained from the centrifugation was transferred into a clean tube and evaporated to dryness using an evaporator at 40° C. under a stream of nitrogen. The residue was reconstituted in 200 μL of water/acetonitrile (50/50, v/v) solvent system, and a 20-μL portion of the aliquot was injected into HPLC system for analysis. For the study, A 100 μL blank plasma from untreated mouse was also processed in the same manner as the treated. The important PK parameters of CZ48 hydrate and CPT in 48 mice were obtained from the HPLC analysis and shown in Table 4.

TABLE 4

The pharmakinetic parameters of hydrated crystalline CZ48 and its major metabolite CPT in mice after oral administration with dose of 2000 mg/kg

| Parameters | Hydrated Crystalline CZ48 | CPT |
|---|---|---|
| $AUC_{0-8}$ (ng · h · ml−1) | — | 136.43 ± 26.94 |
| $AUC_{0-24}$ (ng · h · ml−1) | 1927.66 ± 113.92 | — |
| $AUC_{0-\infty}$ (ng · h · ml−1) | 2233.44 ± 396.05 | 146.70 ± 34.77 |
| $C_{max}$ (ng/mL) | 284.86 ± 85.55 | 42.28 ± 6.72 |
| $T_{max}$ (h) | 2.0 ± 0.0 | 1.0 ± 0.0 |
| $T_{1/2}$ (h) | 8.70 ± 4.18 | 1.87 ± 0.63 |
| $K_e$ (1/h) | 0.09 ± 0.03 | 0.40 ± 0.13 |
| MRT (h) | 11.62 ± 4.34 | 3.36 ± 0.87 |

Example 5

The determination of percentage absorption of crystalline CZ48 hydrate in mouse. Absorption studies were also performed with crystalline camptothecin-20-O-propionate hydrate by using a mouse perfusion procedure on 4 nude mice. Prior to the in situ single-pass perfusion procedure, HBSS buffer (pH 7.4) consisting of 9.801 g/L HBSS powders, 0.372 g/L $NaHCO_3$, 3.502 g/L glucose, 5.963 g/L HEPES, and 1.164 g/L NaCl was prepared and stored in a refrigerator. The perfusate for the procedure was prepared by mixing a certain amount of the drug, crystalline CZ48 hydrate, with an amount of HBSS buffer. The mixture was heated up to 37° C. (body temperature) right before use. A group of 4 mice with weights ranging from 25 to 30 grams and ages ranging from 9 to 11 months were anesthetized and placed onto a heating plate. The plate was maintained a constant temperature of 37° C. After a perfusion system was set ready with a mouse, two segments of the intestine (small intestine, IS, and colon) were simultaneously perfused with the freshly prepared perfusate. The pump was maintained at a constant flow-rate of 0.191 mL/min for the whole perfusion. Two perfusate samples were collected from each outlet (SI tract or colon) every 30 min. The concentrations of the drug in perfusate from the outlets were determined by HPLC analysis, and the corresponding percentage absorptions were calculated relative to the starting amount of the drug and shown in Table 5.

TABLE 5

The results of intestinal perfusion with mice

| Mice | % Crystalline CZ48 Hydrate Absorptions | |
|---|---|---|
| | SI | Colon |
| No. 1 | 16.51 | −35.17 |
| 2 | 9.34 | −73.24 |
| 3 | 45.85 | 6.82 |
| 4 | 11.49 | 8.04 |
| Ave | 22.23 | −19.46 |
| SD | 16.96 | 38.83 |

As shown in Table 5, significant absorptions occurred in the small intestinal tract. The negative percentage absorptions recorded for the colon tract indicates that the amount of the drug coming out of the colon tract was more than the amount initially placed into the mouth tract of the duodenum of the mouse. This might be attributed to the accumulations of the drug in the colon tract due to the multiple absorption/efflux cycles.

Crystal structural determination of crystalline CZ48 hydrate. Single crystal X-ray analysis was done by using a Siemens SMART diffractometer equipped with CCD area detector. A crystal with dimensions of 0.4×0.08×0.02 mm was mounted in glass fiber under a stream of cold nitrogen gas at −60° C. Monochromatic Mo $K_{\alpha 1}$ radiation ($\lambda$=0.71073 Å) was used to collect a full hemisphere of data with the narrow-frame method. The data were integrated using the Siemens SAINT program, and the intensities corrected for Lorentz factor, polarization, air absorption, and absorption due to variation in the path length. Empirical absorption correction was applied and redundant reflections were averaged. Final cell parameters were refined using 1971 reflections having I>10 $\sigma$(I). The tetragonal cell parameters are a=15.008(2) Å, b=6.977(1) Å, c=21.810(3) Å $\beta$=99.959°, V=2249.2(5) Å$^3$, Z=4, $\rho$=1.354 g/cm$^3$, 2$\theta$max=56.66°. The structure was solved by direct methods with space group P2$_1$ (No. 4) and refined by full-matrix least-squares calculations on F$^2$, the thermal motion of all C, N O atoms were treated anisotropically. The final R indices [I>2$\sigma$(I)], R1=0.0454, wR2=0.0763, R indices [all data], R1=0.1105, wR2=0.0933. All calculations were made with using the Siemens SHELXTL programs package. Crystal data and structure refinement for [C$_{23}$H$_{20}$N$_2$O$_5$]·3H$_2$O are shown in Table 7. Atomic coordinates (x10$^4$) and equivalent isotropic displacement parameters (Å$^2$×10$^3$) for [C$_{23}$H$_{20}$N$_2$O$_5$]·3H$_2$O are shown in Table 8. Bond lengths [Å] and angles [°] for [C$_{23}$H$_{20}$N$_2$O$_5$]·3H$_2$O are shown in Table 9. Anisotropic displacement parameters (Å$^2$×10$^3$) for [C$_{23}$H$_{20}$N$_2$O$_5$]·3H$_2$O are shown in Table 10.

TABLE 7

Crystal data and structure refinement for [C$_{23}$H$_{20}$N$_2$O$_5$]·3H$_2$O

| | |
|---|---|
| Identification code | T94 |
| Empirical formula | C23 H26 N2 O8 |
| Formula weight | 458.46 |
| Temperature | 213(2) K |
| Wavelength | 0.71073 Å |
| Crystal system | Monoclinic |
| Space group | P2$_1$ |
| Unit cell dimensions | a = 15.008(2) Å   $\alpha$ = 90°. |
| | b = 6.9769(10) Å   $\beta$ = 99.959(2)°. |
| | c = 21.810(3) Å   $\gamma$ = 90°. |
| Volume | 2249.2(5) Å$^3$ |
| Z | 4 |
| Density (calculated) | 1.354 g/cm$^3$ |
| Absorption coefficient | 0.103 mm$^{-1}$ |
| F(000) | 968 |
| Crystal size | 0.40 × 0.08 × 0.02 mm$^3$ |
| Theta range for data collection | 1.53 to 28.33°. |
| Index ranges | −20 <= h <= 15, −8 <= k <= 9, |
| | −28 <= l <= 21 |
| Reflections collected | 14162 |
| Independent reflections | 14162 [R(int) = 0.0496] |
| Completeness to theta = 28.33° | 95.6% |
| Absorption correction | Empirical |
| Max. and min. transmission | 0.8092 and 0.7004 |
| Refinement method | Full-matrix least-squares on F$^2$ |
| Data/restraints/parameters | 14162/1/633 |
| Goodness-of-fit on F$^2$ | 0.780 |
| Final R indices [I > 2sigma(I)] | R1 = 0.0454, wR2 = 0.0763 |
| R indices (all data) | R1 = 0.1105, wR2 = 0.0933 |

TABLE 7-continued

Crystal data and structure refinement for [C$_{23}$H$_{20}$N$_2$O$_5$]·3H$_2$O

| | |
|---|---|
| Extinction coefficient | 0.00000(11) |
| Largest diff. peak and hole | 0.168 and −0.172 e.Å$^{-3}$ |

TABLE 8

Atomic coordinates (×10$^4$) and equivalent isotropic displacement parameters (Å$^2$ × 10$^3$) for [C$_{23}$H$_{20}$N$_2$O$_5$]·3H$_2$O

| | x | y | z | U(eq) |
|---|---|---|---|---|
| C(1) | −1249(2) | 734(5) | 1218(2) | 45(1) |
| C(2) | −2180(2) | 697(5) | 1137(2) | 51(1) |
| C(3) | −2705(2) | 747(5) | 543(2) | 54(1) |
| C(4) | −2300(2) | 845(5) | 31(2) | 47(1) |
| C(5) | −1338(2) | 864(5) | 89(2) | 37(1) |
| C(6) | −816(2) | 826(4) | 697(2) | 38(1) |
| C(7) | −894(2) | 886(4) | −432(2) | 39(1) |
| C(8) | 27(2) | 877(4) | −327(2) | 33(1) |
| C(9) | 491(2) | 903(4) | 291(1) | 30(1) |
| C(10) | 695(2) | 831(5) | −764(1) | 36(1) |
| C(11) | 1471(2) | 938(4) | 284(2) | 33(1) |
| C(12) | 2388(2) | 759(5) | −528(2) | 35(1) |
| C(13) | 3157(2) | 772(4) | −34(2) | 34(1) |
| C(14) | 3067(2) | 920(4) | 572(1) | 32(1) |
| C(15) | 2199(2) | 993(4) | 744(1) | 35(1) |
| C(16) | 4063(2) | 652(5) | −223(1) | 39(1) |
| C(17) | 4698(2) | −38(5) | 863(2) | 43(1) |
| C(18) | 3920(2) | 1101(5) | 1050(1) | 36(1) |
| C(19) | 4191(2) | 3246(4) | 1112(1) | 39(1) |
| C(20) | 5039(2) | 3639(5) | 1599(2) | 53(1) |
| C(21) | 3547(2) | −1319(5) | 1731(2) | 42(1) |
| C(22) | 3391(2) | −1700(5) | 2375(2) | 55(1) |
| C(23) | 3057(2) | −3713(5) | 2462(2) | 69(1) |
| C(24) | −1296(2) | 7496(5) | 6345(2) | 43(1) |
| C(25) | −2208(2) | 7380(5) | 6318(2) | 50(1) |
| C(26) | −2779(2) | 7338(5) | 5734(2) | 52(1) |
| C(27) | −2434(2) | 7452(5) | 5201(2) | 46(1) |
| C(28) | −1494(2) | 7557(4) | 5214(2) | 33(1) |
| C(29) | −919(2) | 7572(4) | 5799(2) | 34(1) |
| C(30) | −1101(2) | 7601(4) | 4672(2) | 37(1) |
| C(31) | −179(2) | 7612(5) | 4735(2) | 31(1) |
| C(32) | 338(2) | 7628(5) | 5341(2) | 30(1) |
| C(33) | 448(2) | 7597(5) | 4262(1) | 36(1) |
| C(34) | 1296(2) | 7576(5) | 5291(2) | 32(1) |
| C(35) | 2136(2) | 7419(4) | 4429(2) | 35(1) |
| C(36) | 2932(2) | 7290(4) | 4903(2) | 33(1) |
| C(37) | 2901(2) | 7376(4) | 5517(2) | 31(1) |
| C(38) | 2060(2) | 7521(4) | 5730(1) | 33(1) |
| C(39) | 3818(2) | 7072(5) | 4672(2) | 45(1) |
| C(40) | 4509(2) | 6193(5) | 5742(2) | 42(1) |
| C(41) | 3786(2) | 7434(5) | 5964(1) | 32(1) |
| C(42) | 4111(2) | 9549(5) | 6027(1) | 42(1) |
| C(43) | 4985(2) | 9880(5) | 6493(2) | 52(1) |
| C(44) | 3461(2) | 4998(5) | 6663(2) | 37(1) |
| C(45) | 3447(2) | 4602(5) | 7329(2) | 51(1) |
| C(46) | 3242(2) | 2520(5) | 7463(2) | 63(1) |
| N(1) | 120(2) | 881(4) | 797(1) | 38(1) |
| N(2) | 1565(2) | 841(4) | −331(1) | 33(1) |
| N(3) | 17(2) | 7618(4) | 5863(1) | 34(1) |
| N(4) | 1344(2) | 7534(4) | 4668(1) | 31(1) |
| O(1) | 2435(1) | 639(3) | −1088(1) | 44(1) |
| O(2) | 4756(1) | −117(3) | 255(1) | 49(1) |
| O(3) | 5289(2) | −760(3) | 1231(1) | 57(1) |
| O(4) | 3788(1) | 526(3) | 1658(1) | 39(1) |
| O(5) | 3469(1) | −2474(3) | 1308(1) | 54(1) |
| O(6) | 2142(1) | 7384(3) | 3869(1) | 45(1) |
| O(7) | 4502(1) | 6092(3) | 5127(1) | 48(1) |
| O(8) | 5108(1) | 5412(3) | 6091(1) | 55(1) |
| O(9) | 3704(1) | 6866(3) | 6584(1) | 35(1) |
| O(10) | 3291(1) | 3905(3) | 6238(1) | 47(1) |
| O(11) | 998(2) | 8164(4) | 2777(1) | 59(1) |
| O(12) | 1226(2) | 1248(4) | 2025(1) | 56(1) |
| O(13) | 602(2) | 4974(4) | 2037(1) | 68(1) |
| O(14) | 1264(2) | 7001(4) | 7044(2) | 63(1) |

TABLE 8-continued

Atomic coordinates (×10⁴) and equivalent isotropic displacement parameters ($Å^2 \times 10^3$) for [$C_{23}H_{20}N_2O_5$]•$3H_2O$

| | x | y | z | U(eq) |
|---|---|---|---|---|
| O(15) | 802(2) | 3200(5) | 7072(2) | 83(1) |
| O(16) | −1229(3) | 5058(4) | 2183(2) | 59(1) |

U(eq) is defined as one third of the trace of the orthogonalized $U^{ij}$ tensor.

TABLE 9

Bond lengths [Å] and angles [°] for [$C_{23}H_{20}N_2O_5$]•$3H_2O$

| | |
|---|---|
| C(1)—C(2) | 1.378(4) |
| C(1)—C(6) | 1.404(4) |
| C(2)—C(3) | 1.393(5) |
| C(3)—C(4) | 1.362(4) |
| C(4)—C(5) | 1.428(4) |
| C(5)—C(7) | 1.413(4) |
| C(5)—C(6) | 1.418(4) |
| C(6)—N(1) | 1.385(3) |
| C(7)—C(8) | 1.362(4) |
| C(8)—C(9) | 1.407(4) |
| C(8)—C(10) | 1.498(4) |
| C(9)—N(1) | 1.317(4) |
| C(9)—C(11) | 1.473(4) |
| C(10)—N(2) | 1.473(3) |
| C(11)—C(15) | 1.351(4) |
| C(11)—N(2) | 1.375(4) |
| C(12)—O(1) | 1.238(3) |
| C(12)—N(2) | 1.377(3) |
| C(12)—C(13) | 1.437(4) |
| C(13)—C(14) | 1.355(4) |
| C(13)—C(16) | 1.490(4) |
| C(14)—C(15) | 1.418(4) |
| C(14)—C(18) | 1.510(4) |
| C(16)—O(2) | 1.443(3) |
| C(17)—O(3) | 1.199(3) |
| C(17)—O(2) | 1.345(4) |
| C(17)—C(18) | 1.526(4) |
| C(18)—O(4) | 1.433(3) |
| C(18)—C(19) | 1.551(4) |
| C(19)—C(20) | 1.536(4) |
| C(21)—O(5) | 1.215(4) |
| C(21)—O(4) | 1.354(4) |
| C(21)—C(22) | 1.487(4) |
| C(22)—C(23) | 1.515(5) |
| C(24)—C(25) | 1.361(4) |
| C(24)—C(29) | 1.405(4) |
| C(25)—C(26) | 1.409(5) |
| C(26)—C(27) | 1.354(4) |
| C(27)—C(28) | 1.409(4) |
| C(28)—C(30) | 1.408(4) |
| C(28)—C(29) | 1.413(4) |
| C(29)—N(3) | 1.388(3) |
| C(30)—C(31) | 1.368(4) |
| C(31)—C(32) | 1.411(4) |
| C(31)—C(33) | 1.512(4) |
| C(32)—N(3) | 1.311(4) |
| C(32)—C(34) | 1.460(4) |
| C(33)—N(4) | 1.477(3) |
| C(34)—C(38) | 1.362(4) |
| C(34)—N(4) | 1.373(4) |
| C(35)—O(6) | 1.223(3) |
| C(35)—N(4) | 1.380(3) |
| C(35)—C(36) | 1.440(4) |
| C(36)—C(37) | 1.348(4) |
| C(36)—C(39) | 1.508(4) |
| C(37)—C(38) | 1.423(4) |
| C(37)—C(41) | 1.507(4) |
| C(39)—O(7) | 1.468(3) |
| C(40)—O(8) | 1.204(3) |
| C(40)—O(7) | 1.340(4) |
| C(40)—C(41) | 1.531(4) |
| C(41)—O(9) | 1.434(3) |
| C(41)—C(42) | 1.553(4) |

TABLE 9-continued

Bond lengths [Å] and angles [°] for [$C_{23}H_{20}N_2O_5$]•$3H_2O$

| | |
|---|---|
| C(42)—C(43) | 1.532(4) |
| C(44)—O(10) | 1.192(4) |
| C(44)—O(9) | 1.372(4) |
| C(44)—C(45) | 1.483(4) |
| C(45)—C(46) | 1.524(4) |
| C(2)—C(1)—C(6) | 119.8(3) |
| C(1)—C(2)—C(3) | 121.1(3) |
| C(4)—C(3)—C(2) | 120.1(3) |
| C(3)—C(4)—C(5) | 121.0(3) |
| C(7)—C(5)—C(6) | 119.5(3) |
| C(7)—C(5)—C(4) | 122.6(3) |
| C(6)—C(5)—C(4) | 117.9(3) |
| N(1)—C(6)—C(1) | 118.3(3) |
| N(1)—C(6)—C(5) | 121.8(3) |
| C(1)—C(6)—C(5) | 119.9(3) |
| C(8)—C(7)—C(5) | 118.1(3) |
| C(7)—C(8)—C(9) | 118.7(3) |
| C(7)—C(8)—C(10) | 131.8(3) |
| C(9)—C(8)—C(10) | 109.6(3) |
| N(1)—C(9)—C(8) | 126.2(3) |
| N(1)—C(9)—C(11) | 125.2(3) |
| C(8)—C(9)—C(11) | 108.6(3) |
| N(2)—C(10)—C(8) | 102.1(2) |
| C(15)—C(11)—N(2) | 121.3(3) |
| C(15)—C(11)—C(9) | 132.3(3) |
| N(2)—C(11)—C(9) | 106.4(3) |
| O(1)—C(12)—N(2) | 121.2(3) |
| O(1)—C(12)—C(13) | 124.4(3) |
| N(2)—C(12)—C(13) | 114.3(3) |
| C(14)—C(13)—C(12) | 122.0(3) |
| C(14)—C(13)—C(16) | 121.6(3) |
| C(12)—C(13)—C(16) | 116.4(3) |
| C(13)—C(14)—C(15) | 120.8(3) |
| C(13)—C(14)—C(18) | 117.7(3) |
| C(15)—C(14)—C(18) | 121.5(3) |
| C(11)—C(15)—C(14) | 117.7(3) |
| O(2)—C(16)—C(13) | 113.5(3) |
| O(3)—C(17)—O(2) | 118.5(3) |
| O(3)—C(17)—C(18) | 123.5(3) |
| O(2)—C(17)—C(18) | 117.9(3) |
| O(4)—C(18)—C(14) | 112.3(2) |
| O(4)—C(18)—C(17) | 109.7(3) |
| C(14)—C(18)—C(17) | 111.6(3) |
| O(4)—C(18)—C(19) | 105.4(3) |
| C(14)—C(18)—C(19) | 108.6(3) |
| C(17)—C(18)—C(19) | 108.9(3) |
| C(20)—C(19)—C(18) | 114.0(3) |
| O(5)—C(21)—O(4) | 122.3(3) |
| O(5)—C(21)—C(22) | 126.1(3) |
| O(4)—C(21)—C(22) | 111.6(3) |
| C(21)—C(22)—C(23) | 113.2(3) |
| C(25)—C(24)—C(29) | 121.0(3) |
| C(24)—C(25)—C(26) | 119.4(4) |
| C(27)—C(26)—C(25) | 120.9(3) |
| C(26)—C(27)—C(28) | 121.1(3) |
| C(30)—C(28)—C(27) | 123.2(3) |
| C(30)—C(28)—C(29) | 118.6(3) |
| C(27)—C(28)—C(29) | 118.1(3) |
| N(3)—C(29)—C(24) | 117.8(3) |
| N(3)—C(29)—C(28) | 122.6(3) |
| C(24)—C(29)—C(28) | 119.5(3) |
| C(31)—C(30)—C(28) | 118.6(3) |
| C(30)—C(31)—C(32) | 118.5(3) |
| C(30)—C(31)—C(33) | 132.1(3) |
| C(32)—C(31)—C(33) | 109.4(3) |
| N(3)—C(32)—C(31) | 126.0(3) |
| N(3)—C(32)—C(34) | 125.3(3) |
| C(31)—C(32)—C(34) | 108.6(3) |
| N(4)—C(33)—C(31) | 101.6(2) |
| C(38)—C(34)—N(4) | 120.8(3) |
| C(38)—C(34)—C(32) | 132.0(3) |
| N(4)—C(34)—C(32) | 107.1(3) |
| O(6)—C(35)—N(4) | 122.2(3) |
| O(6)—C(35)—C(36) | 124.5(3) |
| N(4)—C(35)—C(36) | 113.2(3) |
| C(37)—C(36)—C(35) | 122.9(3) |
| C(37)—C(36)—C(39) | 121.3(3) |

TABLE 9-continued

Bond lengths [Å] and angles [°] for [C$_{23}$H$_{20}$N$_2$O$_5$]•3H$_2$O

| | |
|---|---|
| C(35)—C(36)—C(39) | 115.8(3) |
| C(36)—C(37)—C(38) | 120.9(3) |
| C(36)—C(37)—C(41) | 117.8(3) |
| C(38)—C(37)—C(41) | 121.2(3) |
| C(34)—C(38)—C(37) | 117.3(3) |
| O(7)—C(39)—C(36) | 112.1(3) |
| O(8)—C(40)—O(7) | 119.0(3) |
| O(8)—C(40)—C(41) | 123.2(3) |
| O(7)—C(40)—C(41) | 117.6(3) |
| O(9)—C(41)—C(37) | 113.2(2) |
| O(9)—C(41)—C(40) | 108.9(3) |
| C(37)—C(41)—C(40) | 111.9(3) |
| O(9)—C(41)—C(42) | 104.9(2) |
| C(37)—C(41)—C(42) | 108.1(3) |
| C(40)—C(41)—C(42) | 109.7(2) |
| C(43)—C(42)—C(41) | 114.9(3) |
| O(10)—C(44)—O(9) | 122.5(3) |
| O(10)—C(44)—C(45) | 127.1(3) |
| O(9)—C(44)—C(45) | 110.4(3) |
| C(44)—C(45)—C(46) | 113.8(3) |
| C(9)—N(1)—C(6) | 115.7(3) |
| C(11)—N(2)—C(12) | 123.8(3) |
| C(11)—N(2)—C(10) | 113.3(2) |
| C(12)—N(2)—C(10) | 122.9(3) |
| C(32)—N(3)—C(29) | 115.6(3) |
| C(34)—N(4)—C(35) | 124.8(3) |
| C(34)—N(4)—C(33) | 113.2(2) |
| C(35)—N(4)—C(33) | 122.0(3) |
| C(17)—O(2)—C(16) | 122.4(2) |
| C(21)—O(4)—C(18) | 117.1(3) |
| C(40)—O(7)—C(39) | 122.4(2) |
| C(44)—O(9)—C(41) | 116.6(2) |

Symmetry transformations used to generate equivalent atoms:

TABLE 10

Anisotropic displacement parameters (Å$^2$ × 10$^3$) for [C$_{23}$H$_{20}$N$_2$O$_5$]•3H$_2$O

| | U$^{11}$ | U$^{22}$ | U$^{33}$ | U$^{23}$ | U$^{13}$ | U$^{12}$ |
|---|---|---|---|---|---|---|
| C(1) | 45(2) | 43(2) | 48(2) | −1(2) | 9(2) | 1(2) |
| C(2) | 51(2) | 51(3) | 55(3) | −2(2) | 18(2) | −4(2) |
| C(3) | 44(2) | 45(2) | 73(3) | −7(2) | 12(2) | −4(2) |
| C(4) | 41(2) | 38(2) | 59(3) | −3(2) | −4(2) | −1(2) |
| C(5) | 38(2) | 24(2) | 46(2) | −4(2) | 2(2) | −7(2) |
| C(6) | 40(2) | 25(2) | 48(2) | 2(2) | 9(2) | 2(2) |
| C(7) | 45(2) | 28(2) | 40(2) | 0(2) | −7(2) | −6(2) |
| C(8) | 39(2) | 24(2) | 34(2) | −2(2) | 2(2) | −5(2) |
| C(9) | 39(2) | 19(2) | 31(2) | 1(2) | 6(2) | 1(2) |
| C(10) | 44(2) | 28(2) | 32(2) | 1(2) | −3(2) | −5(2) |
| C(11) | 39(2) | 29(2) | 31(2) | 3(2) | 4(2) | 1(2) |
| C(12) | 43(2) | 35(2) | 27(2) | 1(2) | 7(2) | −7(2) |
| C(13) | 37(2) | 28(2) | 36(2) | 2(2) | 5(2) | 2(2) |
| C(14) | 38(2) | 27(2) | 28(2) | −4(2) | 2(2) | 1(2) |
| C(15) | 44(2) | 34(2) | 24(2) | 3(2) | 2(2) | 6(2) |
| C(16) | 42(2) | 45(2) | 28(2) | −1(2) | 4(2) | −3(2) |
| C(17) | 40(2) | 41(2) | 44(2) | −6(2) | −1(2) | 2(2) |
| C(18) | 35(2) | 43(2) | 28(2) | 2(2) | 1(2) | 4(2) |
| C(19) | 40(2) | 38(2) | 35(2) | −4(2) | −1(2) | 0(2) |
| C(20) | 54(2) | 53(3) | 47(2) | −4(2) | −6(2) | −6(2) |
| C(21) | 39(2) | 44(3) | 40(2) | 4(2) | −1(2) | 4(2) |
| C(22) | 64(3) | 60(3) | 40(2) | 14(2) | 11(2) | 9(2) |
| C(23) | 63(3) | 72(3) | 75(3) | 19(3) | 20(2) | 2(2) |
| C(24) | 47(2) | 38(2) | 45(2) | 1(2) | 10(2) | 3(2) |
| C(25) | 43(2) | 50(2) | 61(3) | 1(2) | 18(2) | 0(2) |
| C(26) | 39(2) | 43(2) | 73(3) | 0(2) | 5(2) | 1(2) |
| C(27) | 41(2) | 34(2) | 58(3) | 0(2) | −2(2) | 1(2) |
| C(28) | 35(2) | 21(2) | 42(2) | −2(2) | −1(2) | 1(2) |
| C(29) | 36(2) | 24(2) | 42(2) | 3(2) | 4(2) | 1(2) |
| C(30) | 48(2) | 22(2) | 33(2) | 2(2) | −11(2) | 2(2) |
| C(31) | 34(2) | 23(2) | 34(2) | −1(2) | −2(2) | 1(2) |
| C(32) | 32(2) | 24(2) | 33(2) | 3(2) | 1(2) | 0(2) |
| C(33) | 46(2) | 28(2) | 33(2) | 2(2) | 0(2) | −3(2) |
| C(34) | 42(2) | 23(2) | 30(2) | −2(2) | 2(2) | 1(2) |

TABLE 10-continued

Anisotropic displacement parameters (Å$^2$ × 10$^3$) for [C$_{23}$H$_{20}$N$_2$O$_5$]•3H$_2$O

| | U$^{11}$ | U$^{22}$ | U$^{33}$ | U$^{23}$ | U$^{13}$ | U$^{12}$ |
|---|---|---|---|---|---|---|
| C(35) | 50(2) | 22(2) | 32(2) | 0(2) | 7(2) | 1(2) |
| C(36) | 41(2) | 27(2) | 31(2) | 2(2) | 8(2) | 1(2) |
| C(37) | 33(2) | 23(2) | 35(2) | 0(2) | 2(2) | 0(2) |
| C(38) | 39(2) | 30(2) | 28(2) | −2(2) | 4(2) | 1(2) |
| C(39) | 46(2) | 48(2) | 41(2) | 6(2) | 6(2) | 0(2) |
| C(40) | 43(2) | 42(2) | 43(2) | 2(2) | 12(2) | 2(2) |
| C(41) | 35(2) | 36(2) | 26(2) | 3(2) | 7(2) | 5(2) |
| C(42) | 42(2) | 37(2) | 44(2) | 0(2) | 1(2) | −5(2) |
| C(43) | 51(2) | 54(2) | 49(2) | −6(2) | 4(2) | −9(2) |
| C(44) | 37(2) | 41(2) | 31(2) | 4(2) | 3(2) | 10(2) |
| C(45) | 61(2) | 50(2) | 44(2) | 8(2) | 13(2) | 2(2) |
| C(46) | 70(3) | 64(3) | 55(3) | 17(2) | 9(2) | −7(2) |
| N(1) | 39(2) | 31(2) | 43(2) | 1(2) | 6(1) | −4(1) |
| N(2) | 35(2) | 32(2) | 30(2) | −1(1) | 1(1) | −4(1) |
| N(3) | 38(2) | 26(2) | 36(2) | 0(1) | 4(1) | 2(1) |
| N(4) | 36(2) | 28(2) | 28(2) | 2(1) | 1(1) | 0(1) |
| O(1) | 47(1) | 52(2) | 33(1) | 1(1) | 2(1) | −4(1) |
| O(2) | 43(2) | 67(2) | 37(2) | 0(1) | 5(1) | 15(1) |
| O(3) | 49(2) | 68(2) | 50(2) | 0(1) | −3(1) | 23(1) |
| O(4) | 44(1) | 41(2) | 32(1) | 1(1) | 4(1) | 2(1) |
| O(5) | 78(2) | 40(2) | 40(2) | 0(1) | 3(1) | 2(1) |
| O(6) | 57(2) | 52(2) | 26(1) | −1(2) | 8(1) | 3(1) |
| O(7) | 45(1) | 63(2) | 38(2) | 3(1) | 14(1) | 13(1) |
| O(8) | 47(2) | 68(2) | 49(2) | 5(1) | 7(1) | 22(1) |
| O(9) | 39(1) | 33(1) | 32(1) | −2(1) | 4(1) | 1(1) |
| O(10) | 62(2) | 43(2) | 34(2) | −5(1) | 2(1) | 3(1) |
| O(11) | 63(2) | 58(2) | 48(2) | −2(2) | −10(2) | −1(2) |
| O(12) | 62(2) | 64(2) | 38(2) | 2(1) | 1(1) | −1(2) |
| O(13) | 58(2) | 69(2) | 73(2) | −6(2) | 1(2) | 9(2) |
| O(14) | 63(2) | 70(3) | 52(2) | 12(2) | 0(1) | 2(2) |
| O(15) | 59(2) | 89(2) | 94(3) | 24(2) | −5(2) | 1(2) |
| O(16) | 67(2) | 59(3) | 46(2) | −2(2) | 0(1) | 2(2) |

The anisotropic displacement factor exponent takes the form: $-2\pi^2[h^2a^{*2}U^{11}+\ldots+2\,h\,k\,a^*\,b^*\,U^{12}]$ It is clear from these studies, that the compounds of the present invention demonstrate an astonishing level of anti-cancer activity. This applies both to the spectrum of tumors covered and to the quality of the responses. The method of the present invention has been able to block growth completely and to totally regress human xenografts of carcinomas (e.g., lung, breast, colon, stomach, pancreas, bladder, prostate, osteosarcoma and ovaries) and malignant melanomas. This was accomplished without any observable toxicity. Many of the mammals which were treated continuously for six months showed no ill effects nor regrowth of the tumor they once carried. The hydrated crystalline aliphatic ester hydrates of the present invention should all have about the same degree of efficacy and therapeutic index values.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A crystalline camptothecin hydrate of formula (I):

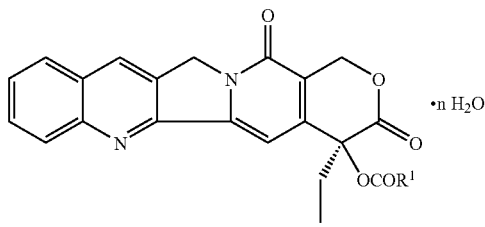

wherein n is a number ranging from 1 to 10, and $R^1$ is $C_2$-$C_6$ alkyl group.

2. The crystalline camptothecin hydrate of claim 1, wherein $R_1$ is a linear $C_2$-$C_4$ alkyl group.

3. The crystalline camptothecin hydrate of claim 1, wherein $R_1$ is ethyl.

4. The crystalline camptothecin hydrate of claim 3, wherein the crystalline camptothecin hydrate has a melting point of from about 240° C. to about 243° C.

5. The crystalline camptothecin hydrate of claim 3, wherein the compound has a melting point of about 242° C.

6. The crystalline camptothecin hydrate of claim 1, wherein the compound has a purity of about 99% to about 100%.

7. The crystalline camptothecin hydrate of claim 1, wherein n is a number ranging from 1 to 3.

8. A method for treating a cancer or a malignant tumor in a patient comprising administering a composition comprising an effective amount of the crystalline camptothecin hydrate of claim 1, wherein said cancer or malignant tumor is responsive to said composition, wherein said cancer is bladder cancer, breast cancer, colon cancer, desmoplastic small round cell tumor (DSRCT), kidney cancer, melanoma. lung cancer, pancreatic cancer, or prostate cancer.

9. The method of claim 8, wherein $R^1$ is ethyl.

10. The method of claim 8, wherein said cancer is pancreatic cancer.

11. The method of claim 10, wherein $R^1$ is ethyl.

12. The method of claim 8, wherein the crystalline camptothecin hydrate is administered intravenously, intramuscularly, or transdermally.

13. The method of claim 8, wherein the crystalline camptothecin hydrate is administered orally.

14. A pharmaceutical composition comprising an effective amount of the crystalline camptothecin hydrate of claim 1 and a pharmaceutically acceptable carrier.

15. The pharmaceutical composition of claim 14, wherein the carrier is a lipid or a lipid-like emulsifier.

16. The crystalline camptothecin hydrate of claim 1, wherein said crystalline camptothecin hydrate has a therapeutic index of from 2 to 500, as determined by administering said crystalline camptothecin hydrate to nude mice having a tumor xenograft, when 2,000 mg/kg is used as the highest tolerated dose.

17. The crystalline camptothecin hydrate of claim 16, wherein said therapeutic index is from 10 to 100.

18. The crystalline camptothecin hydrate of claim 1, wherein the crystalline camptothecin hydrate has a monoclinic system with sizes of (0.10 to 0.50) ×(0.01 to 0.10) × (0.01 to 0.05) mm³ and volumes of from 100 to 5000 Å³.

19. The crystalline camptothecin hydrate of claim 18, wherein said crystalline camptothecin hydrate is crystalline camptothecin-20-propionate hydrate.

* * * * *